(12) United States Patent  (10) Patent No.: US 9,081,022 B2
Runyon et al.  (45) Date of Patent: Jul. 14, 2015

(54) CENTRIFUGE ROTOR FOR SEPARATION AND PROCESSING OF COMPLEX FLUIDS

(75) Inventors: Matthew K. Runyon, East Grand Rapids, MI (US); Daniel M. Mueth, Chicago, IL (US); Sergio O. Guevara, Chicago, IL (US); Haojun Fu, Naperville, IL (US)

(73) Assignee: ARRYX, INC., Braintree, MA (US)

( * ) Notice: Subject to any disclaimer, the term of this patent is extended or adjusted under 35 U.S.C. 154(b) by 812 days.

(21) Appl. No.: 13/363,938

(22) Filed: Feb. 1, 2012

(65) Prior Publication Data

US 2012/0202673 A1   Aug. 9, 2012

Related U.S. Application Data

(60) Provisional application No. 61/438,571, filed on Feb. 1, 2011, provisional application No. 61/438,645, filed on Feb. 1, 2011.

(51) Int. Cl.
  *G01N 33/80* (2006.01)
  *G01N 21/07* (2006.01)
  *B04B 5/04* (2006.01)
(52) U.S. Cl.
  CPC *G01N 33/80* (2013.01); *B04B 5/04* (2013.01); *G01N 21/07* (2013.01)
(58) Field of Classification Search
  CPC .......... G01N 33/80; G01N 21/07; B04B 1/00; B04B 5/04
  See application file for complete search history.

(56) References Cited

U.S. PATENT DOCUMENTS

| | | | |
|---|---|---|---|
| 4,297,104 | A | 10/1981 | Claude |
| 4,608,246 | A | 8/1986 | Bayer et al. |
| 4,816,413 | A | 3/1989 | Sinor et al. |
| 5,256,376 | A | 10/1993 | Callan et al. |
| 5,631,166 | A | 5/1997 | Jewell |
| 6,303,390 | B1 | 10/2001 | Den Boer et al. |
| 6,506,344 | B1 | 1/2003 | Fickenscher et al. |
| 6,935,567 | B2 | 8/2005 | Saga et al. |
| 2010/0178656 | A1 | 7/2010 | Buffiere et al. |
| 2010/0256005 | A1 | 10/2010 | Petrik et al. |
| 2012/0202225 | A1 | 8/2012 | Knutson et al. |

FOREIGN PATENT DOCUMENTS

EP   1008844 A1   6/2000

OTHER PUBLICATIONS

International Search Report and Written Opinion, International Application No. PCT/US2012/023503, dated May 4, 2012.

(Continued)

*Primary Examiner* — Timothy Cleveland
(74) *Attorney, Agent, or Firm* — Lando & Anastasi LLP

(57) ABSTRACT

A rotor is provided for use in a centrifuge system configured to spin the rotor for separating complex fluids. The rotor includes a housing configured to be secured by the centrifuge system and several chambers formed in the housing. Each chamber includes a first chamber portion having a port formed therein and a second chamber portion in fluid communication with the port of the first chamber portion. The second chamber portion may be disposed generally below the port of the first chamber portion. Other rotor designs and methods for separating complex fluids are further disclosed.

9 Claims, 19 Drawing Sheets

(56) References Cited

OTHER PUBLICATIONS

Amasia, M. et al., "Large-volume centrifugal micorfluidic device for blood plasma separation", Research Article, Special Focus: Microfluidics, Bioanalysis (2010), vol. 2, No. 10, pp. 1701-1710.

Zhang, J. et al., "A lab-on-CD prototype for high-speed blood separation", IOP Publishing, Journal of Micromechanics and Microengineering, 18 (2008), 125025 (6pps).

Haeberle, S. et al., "Centrifugal extraction of plasma from whole blood on a rotating disk", Lab on a Chip, 2006, 6, pp. 776-781.

Lee, B.S. et al., "A fully automated immunoassay from whole blood on a disc", Lab on a Chip, 2009, 9, pp. 1548-1555.

International Search Report and Written Opinion, International Application No. PCT/US2012/23553 mailed Aug. 10, 2012.

Campbell, C.J., et al., "Cell Interaction Microarray for Blood Penotyping", Anal. Chem., 2006, 78, 1930-1938.

Extended European Search Report from corresponding European Application No. 12742453.9 dated Feb. 18, 2015.

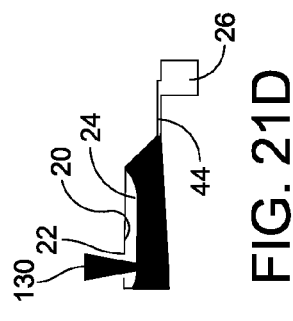
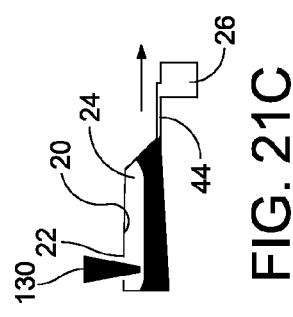
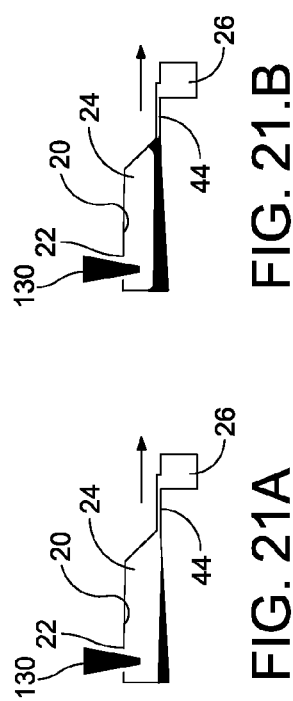
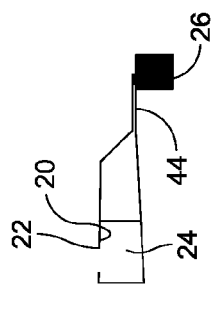
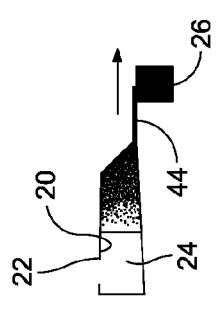
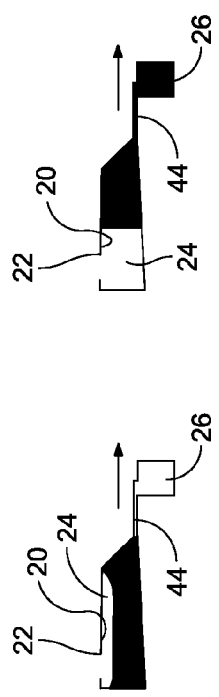
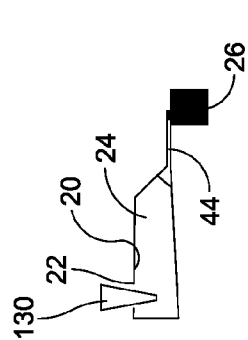
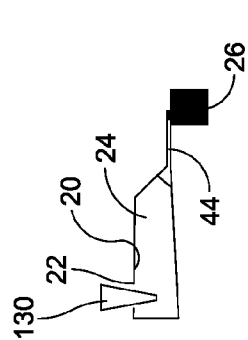
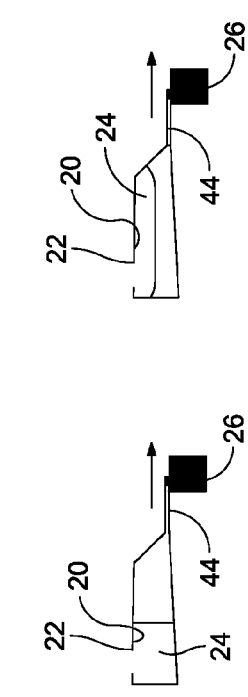
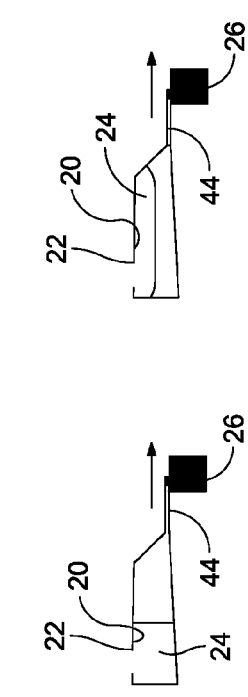

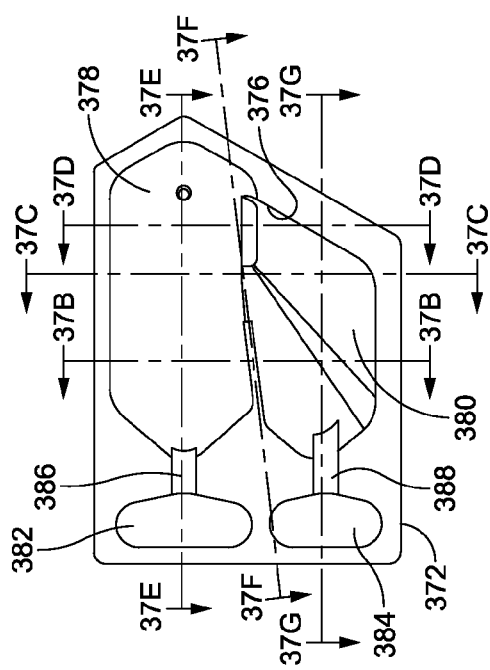

CENTRIFUGE ROTOR FOR SEPARATION AND PROCESSING OF COMPLEX FLUIDS

RELATED APPLICATION

This application claims the benefit of priority under 35 U.S.C. §119(e) to U.S. Provisional Application No. 61/438,571, entitled "CENTRIFUGE ROTOR FOR SEPARATION AND PROCESSING OF COMPLEX FLUIDS," and to U.S. Provisional Application Ser. No. 61/438,645, entitled "METHODS AND DEVICES FOR IMMUNODIAGNOSTIC APPLICATIONS," both of which were filed Feb. 1, 2011. The contents of the aforesaid applications are hereby incorporated by reference in their entirety.

BACKGROUND OF DISCLOSURE

1. Field of Disclosure

Embodiments of the disclosure relate generally to techniques for separating whole blood, and more particularly to a system and method utilizing a rotor and a centrifuge to separate whole blood into plasma and blood cell fractions, as well as other complex fluids.

2. Discussion of Related Art

The use of rotors or discs and centrifuges to separate whole blood is well known. The rotor is configured to receive a sample of whole blood, and upon the performance of a centrifuge operation, plasma is separated from red blood cells. With one known rotor, a sample of whole blood is delivered into a metering chamber through an inlet. The metering chamber includes an overflow channel and a vent. A drain channel connects the metering chamber to a decant region, which comprises two chambers separated from one another such that overflow from a first, separation, chamber spills into a second, plasma, chamber. The arrangement is such that when a centrifuge operation takes place, whole blood travels from the metering chamber to the separation chamber by way of the drain channel. The spinning of the rotor results in red blood cells being separated from the whole blood so that the red blood cells are disposed at the bottom of the first, separation chamber. Once completely separated, plasma rests on top of the red blood cells, and any excess plasma provided in the first chamber spills into the second chamber. One limitation of this type of rotor is that it does not provide a mechanism for withdrawal of the plasma from the rotor.

Other rotor designs suffer from the same limitation as the aforementioned rotor design. The plasma is trapped within the rotor, with no mechanism to withdraw the plasma after it has been isolated. Another difficulty presented by some rotor designs is that a seal may be required between a device, such as a pipette, used to inject whole blood into the rotor and to extract plasma from the rotor. Thus, these rotors do not interface with traditional liquid handling systems, such as those used for diagnostic testing. With nearly all rotors, the plasma must be moved to a second chamber prior to use. Moreover, most rotors use hydrophilic and/or hydrophobic patterning or some other type of valve to control red blood cell and plasma separation.

SUMMARY OF DISCLOSURE

An aspect of the present disclosure is directed to a rotor for use in a centrifuge system configured to spin the rotor. In one embodiment, the rotor comprises a housing configured to be secured by the centrifuge system and at least one chamber formed in the housing. The at least one chamber includes a first chamber portion having a port formed therein and a second chamber portion in fluid communication with the port of the first chamber portion. In one embodiment, the second chamber portion is disposed generally below the port of the first chamber portion.

Embodiments of the rotor include disposing the first chamber portion of the at least one chamber inboard with respect to the second chamber portion of the at least one chamber on the rotor. The first chamber portion may include a top wall that slopes downwardly to the port of the first chamber portion. The first chamber portion of the at least one chamber includes an inlet/outlet opening configured to receive a complex fluid. The inlet/outlet opening and the first chamber portion are configured to receive the complex fluid without requiring a seal between a dispenser containing complex fluid and the housing. The first chamber portion and the second chamber portion are configured so that when a centrifuge operation takes place, a first complex fluid component is substantially retained in the first chamber portion and a second complex fluid component is substantially retained in the second chamber portion. The second chamber portion has a capacity greater than an amount of the second complex fluid component retained in the second chamber portion.

The first chamber portion may include a bottom wall that slopes upwardly to the port of the first chamber portion. The inlet/outlet opening and the first chamber portion are configured to receive the complex fluid without requiring a seal between a dispenser containing complex fluid and the housing. The first chamber portion and the second chamber portion are configured so that when a centrifuge operation takes place, a first complex fluid component is substantially retained in the first chamber portion and a second complex fluid component is retained in the second chamber portion. The second chamber portion has a capacity greater than an amount of the second complex fluid component retained in the second chamber portion. The first chamber portion may include an outlet channel, with the bottom wall being configured to direct fluid or components of the complex fluid to the outlet channel.

The rotor may further include a channel configured to provide fluid communication from the port of the first chamber portion to a port of the second chamber portion. The channel may be configured to provide a barrier between first chamber portion and the second chamber portion. The second chamber portion may include a vent channel. The housing includes a top and a bottom secured to the top, the top defining a top wall of the first chamber portion and a top wall of the second chamber portion, and the bottom defining a bottom wall of the first chamber portion and a bottom wall of the second chamber portion and the top and bottom defining side walls extending between the top wall and the bottom wall. The rotor may further comprise a plurality of chambers radially and symmetrically arranged on the rotor. The first chamber portion and the second chamber portion extend along a radial axis of the rotor.

Another aspect of the disclosure is directed to a rotor comprising a housing configured to be secured by the centrifuge system and the at least one chamber formed in the housing. The at least one chamber includes a first chamber portion having a port formed therein and a second chamber portion in fluid communication with the port of the first chamber portion. The first chamber portion and the second chamber portion are configured so that when a centrifuge operation takes place, a first complex fluid component is retained in the first chamber portion and a second complex fluid component is retained in the second chamber portion. In one embodiment, the second chamber portion has a capacity greater than an amount of the second complex fluid component retained in the second chamber portion.

Yet another aspect of the disclosure is directed to a rotor comprising a housing configured to be secured by the centrifuge system and at least one chamber formed in the housing. The at least one chamber includes a first chamber portion having an opening formed therein to receive a complex fluid, a channel in fluid communication with the first chamber portion, and a second chamber portion in fluid communication with the channel. In one embodiment, the channel is configured so that when a centrifuge operation takes place, a first complex fluid component is retained in the first chamber portion and a second complex fluid component is retained in the second chamber portion.

A further aspect of the disclosure is directed to a rotor comprising a housing configured to be secured by the centrifuge system and at least one chamber formed in the housing. The at least one chamber includes a first chamber portion having a port formed therein and a second chamber portion in fluid communication with the port of the first chamber portion. In one embodiment, the first chamber portion has a capacity greater than an amount of complex fluid to be sampled. In one embodiment, the first chamber portion and the second chamber portion are configured so that when a centrifuge operation takes place, a first complex fluid component is retained in the first chamber portion and a second complex fluid component is retained in the second chamber portion.

Another aspect of the disclosure is directed to a method of separating complex fluids. In one embodiment, the method comprises: providing a rotor including a housing configured to be secured by the centrifuge system, and the at least one chamber formed in the housing, the at least one chamber including a first chamber portion having a port formed therein and a second chamber portion in fluid communication with the port of the first chamber portion, the second chamber portion being disposed generally below the port of the first chamber portion; filling the at least one chamber with a complex fluid; spinning the rotor to separate the complex fluid in the at least one chamber in such a manner that a first complex fluid component is retained in the first chamber portion and a second complex fluid component is retained in the second chamber portion; and extracting the first complex fluid component from the first chamber portion.

Embodiments of the method include filling the at least one chamber and extracting the first complex fluid component with a device, such as a pipette. The device is inserted into an inlet/outlet opening formed in the housing of the rotor without a seal between the device and the housing of the rotor.

A further aspect of the disclosure is directed to a method of separating complex fluids comprising: providing a rotor including a housing configured to be secured by the centrifuge system, and at least one chamber formed in the housing, the at least one chamber including a first chamber portion having a port formed therein and a second chamber portion in fluid communication with the port of the first chamber portion, the first chamber portion and the second chamber portion being configured so that when spinning the rotor, a first complex fluid component is retained in the first chamber portion and a second complex fluid component is retained in the second chamber portion, the second chamber portion having a capacity greater than an amount of the second complex fluid component retained in the second chamber portion; at least partially filling the at least one chamber with a complex fluid; spinning the rotor to separate the complex fluid; and extracting the first complex fluid component from the first chamber portion.

Another aspect of the disclosure is directed to a rotor assembly for use in a centrifuge system configured to spin the rotor assembly. In one embodiment, the rotor assembly comprises a rotor having a housing configured to be secured by the centrifuge system and at least one receptacle formed in the housing, and at least one sample container configured to be disposed within the at least one receptacle of the housing of the rotor.

Embodiments of the rotor assembly may include providing the at least one sample container with a first chamber portion, a second chamber portion, and a channel providing fluid communication between the first chamber portion and the second chamber portion. The second chamber portion may be disposed generally below at least a portion the channel connecting the first chamber portion and the second chamber portion. The first chamber portion may be disposed inboard with respect to the second chamber portion. The first chamber portion may include a cover configured to cover the sample container, the cover having an inlet/outlet configured to receive a complex fluid. The first chamber portion and the second chamber portion of the sample container may be configured so that when a centrifuge operation takes place, a first complex fluid component is substantially retained in the first chamber portion and a second complex fluid component is substantially retained in the second chamber portion.

In one embodiment, the at least one sample container includes a first inlet chamber portion, a first outlet chamber portion, a first channel providing fluid communication between the first inlet chamber portion and the first outlet chamber portion, a second inlet chamber portion in fluid communication with the first inlet chamber portion, a second outlet chamber portion, and a second channel providing fluid communication between the second inlet chamber portion and the second outlet chamber portion.

Still other aspects, embodiments, and advantages of these exemplary aspects and embodiments, are discussed in detail below. Any embodiment disclosed herein may be combined with any other embodiment in any manner consistent with at least one of the objects, aims, and needs disclosed herein, and references to "an embodiment," "some embodiments," "an alternate embodiment," "various embodiments," "one embodiment" or the like are not necessarily mutually exclusive and are intended to indicate that a particular feature, structure, or characteristic described in connection with the embodiment may be included in at least one embodiment. The appearances of such terms herein are not necessarily all referring to the same embodiment. The accompanying drawings are included to provide illustration and a further understanding of the various aspects and embodiments, and are incorporated in and constitute a part of this specification. The drawings, together with the remainder of the specification, serve to explain principles and operations of the described and claimed aspects and embodiments.

BRIEF DESCRIPTION OF DRAWINGS

Various aspects of at least one embodiment are discussed below with reference to the accompanying figures, which are not intended to be drawn to scale. Where technical features in the figures, detailed description or any claim are followed by references signs, the reference signs have been included for the sole purpose of increasing the intelligibility of the figures, detailed description, and claims. Accordingly, neither the reference signs nor their absence are intended to have any limiting effect on the scope of any claim elements. In the figures, each identical or nearly identical component that is illustrated in various figures is represented by a like numeral. For purposes of clarity, not every component may be labeled in every figure. The figures are provided for the purposes of illustration and explanation and are not intended as a definition of the limits of the invention. In the figures:

FIGS. 21A-21D are schematic side views showing the sequence of filling an exemplary chamber of the rotor with a complex fluid;

FIGS. 22A-22D are schematic views showing the sequence of spinning the exemplary chamber of the rotor;

FIGS. 23A-23D are schematic views showing the sequence of relaxing and removing the fluid in the exemplary chamber of the rotor.

FIG. 37A is a top plan view of the disposable sample container shown in FIG. 36;

FIG. 37B is a cross-sectional view taken along line 37B-37B in FIG. 37A;

FIG. 37C is a cross-sectional view taken along line 37C-37C in FIG. 37A;

FIG. 37D is a cross-sectional view taken along line 37D-37D in FIG. 37A;

FIG. 37E is a cross-sectional view taken along line 37E-37E in FIG. 37A;

FIG. 37F is a cross-sectional view taken along line 37F-37F in FIG. 37A; and

FIG. 37G is a cross-sectional view taken along line 37G-37G in FIG. 37A.

DETAILED DESCRIPTION

Figure 1:
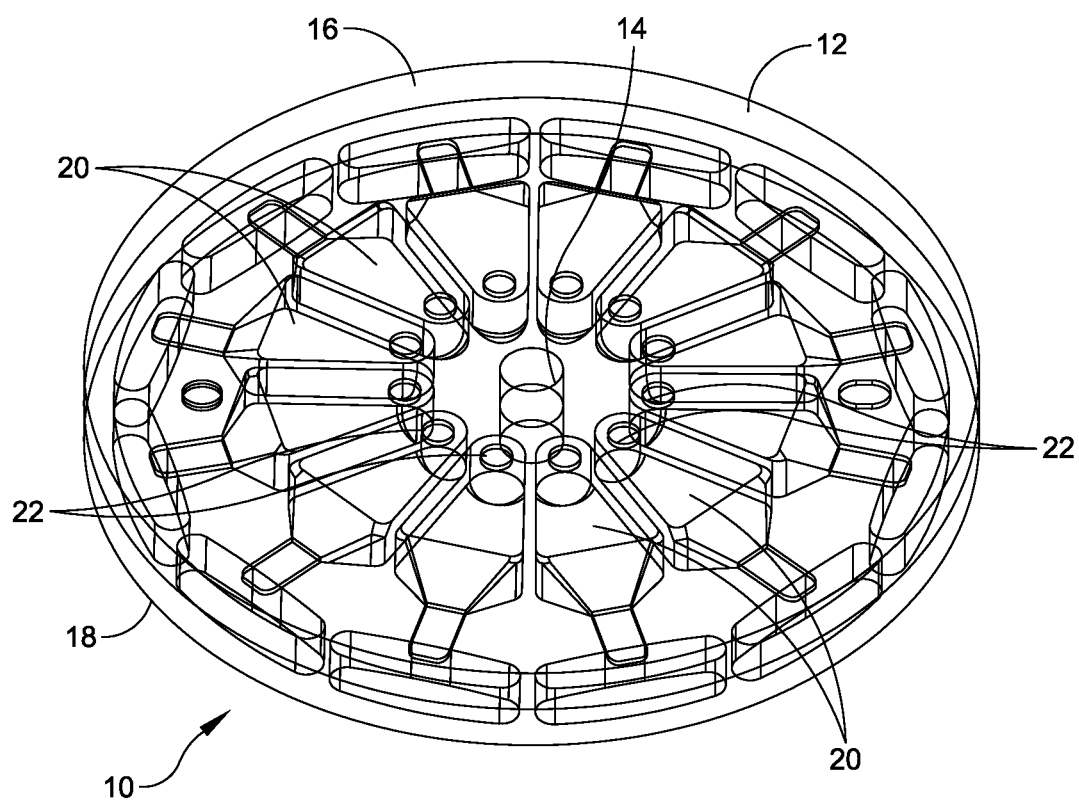
FIG. 1 is a perspective view of a rotor of an embodiment of the disclosure.

It is to be appreciated that embodiments of the systems and methods discussed herein are not limited in application to the details of construction and the arrangement of components set forth in the following description or illustrated in the accompanying drawings. The methods and apparatuses are capable of implementation in other embodiments and of being practiced or of being carried out in various ways. Examples of specific implementations are provided herein for illustrative purposes only and are not intended to be limiting.

In particular, acts, elements and features discussed in connection with any one or more embodiments are not intended to be excluded from a similar role in any other embodiments.

Also, the phraseology and terminology used herein is for the purpose of description and should not be regarded as limiting. Any references to embodiments or elements or acts of the systems and methods herein referred to in the singular may also embrace embodiments including a plurality of these elements, and any references in plural to any embodiment or element or act herein may also embrace embodiments including only a single element. References in the singular or plural form are not intended to limit the presently disclosed systems or methods, their components, acts, or elements. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms. Any references to front and back, left and right, top and bottom, upper and lower, and vertical and horizontal are intended for convenience of description, not to limit the present systems and methods or their components to any one positional or spatial orientation.

As used herein, a "complex fluid" refers to a fluid or solution comprising multiple constituents wherein the constituents may behave differently or become at least partly separated under centrifugation. For example, whole blood is a complex fluid comprising blood plasma and different types of blood cells. Under centrifugation, the cellular components may separate at least partly from the bulk of the plasma, and the cellular components may separate at least partly from dissimilar cellular components (e.g., red cells from platelets). As another example, plasma may be considered a complex fluid insofar as it is contains proteins and fats which may be isolated, enriched, or depleted in part through centrifugation.

A "complex fluid component", as used herein, refers to a single constituent of the complex fluid or a combination of constituents of the complex fluid which is distinct in composition from the unprocessed complex fluid prior to centrifugation. For example, a complex fluid component may be whole blood wherein some of the plasma has been depleted. As another example, a complex fluid component may be whole blood wherein some or all of the cellular components have been at least partially depleted.

Embodiments of the present disclosure are directed to a rotor that is used in a centrifuge system. The rotor includes a housing fabricated from a lightweight material, such as plastic. In one embodiment, the housing is generally disc-shaped, and includes a central opening that is configured to be secured to the centrifuge. The rotor may be further configured with alignment features that enable the rotor to be registered in a specific orientation with respect to the centrifuge system for indexing the position of the rotor. The rotor is configured with one or more chambers, e.g., twelve, each chamber receiving a sample of whole blood, or some other type of complex fluid, e.g., biological fluid, requiring separation. The arrangement is such that the centrifuge spins the rotor to separate plasma from blood cells contained within the whole blood. In a certain embodiment, each chamber includes a first chamber portion having an opening that serves as an inlet/outlet opening for the chamber and a second chamber portion in fluid communication with the first chamber portion. The first chamber portion has a port formed therein, with the second chamber portion being in fluid communication with the port of the first chamber portion. In a particular embodiment, a portion of the second chamber portion is disposed generally below the port of the first chamber portion. This construction ensures that when a centrifuge operation takes place, blood cells are retained in the second chamber portion and plasma is retained in the first chamber portion. Thus, the blood cells are retained in the second chamber portion, both during and after the relaxation and removal of the plasma within the first chamber portion. In another embodiment, the first chamber portion and the second chamber portion extend along a radial axis of the rotor. The first chamber portion and the second chamber portion are configured so that when a centrifuge operation takes place, a first complex fluid component (e.g., plasma) is retained in the first chamber portion and a second complex fluid component (e.g., blood cells and a small amount of associated plasma) is retained in the second chamber portion. The second chamber portion has a capacity greater than an amount of the second complex fluid component retained in the second chamber portion. In yet another embodiment, a channel provides fluid communication between the first chamber portion and the second chamber portion. The channel is configured so that when a centrifuge operation takes place, a first complex fluid component is retained in the first chamber portion and a second complex fluid component is retained in the second chamber portion.

Turning now to the drawings, and more particularly to FIG. 1, a rotor, generally indicated at 10, is provided to spin samples of biological fluids, such as anti-coagulated whole blood, requiring separation. As shown, the rotor 10 includes a disc-shaped body or housing 12 having a central opening 14 formed therein that is configured to be secured to and spun on a centrifuge system (not shown). The housing 12 includes a top half 16 and a bottom half 18 that are secured to one another at every location in which the top half contacts the bottom half. The top half 16 and the bottom half 18 of the housing 12 may be fabricated from any suitable material, such as plastic. The housing 12 may be transparent or translucent so that an operator of the centrifuge system may visually identify or otherwise inspect the samples being processed by the rotor 10. In one embodiment, the top and bottom halves 16, 18 of the housing 12 are secured to one another by any type of joining method, such as ultrasonic welding, laser welding, or some other technique suitable for joining plastic.

Centrifuge systems are well-known in the art, and may include and are not limited to centrifuges offered by Eppendorf North America, Inc. of Westbury, N.Y. under the brand names MiniSpin® and MiniSpin® plus. In one embodiment, the centrifuge system includes an assembly (not shown), which includes a frame or axle designed to receive a rotor, such as rotor 10, thereon to spin the rotor. The axle may be configured to spin on a bearing element, which is driven by an electric drive motor that is coupled to the axle to rotate the axle about an axis. The motor may be capable of rotating the axle in either clockwise or counterclockwise directions, depending upon commands issued by a controller of the centrifuge system. The rotor spins about an axis that is generally aligned with the axis of rotation of the axle.

Samples of complex fluids are received within one or more chambers, each generally indicated at 20, provided in the rotor. In the shown embodiment, there are twelve chambers 20 provided in the rotor 10. However, it should be understood by those skilled in the art, given the benefit of the disclosure, that any number of chambers may be provided so long as the rotor remains in balance while spinning. When a centrifuge operation takes place, the complex fluids are separated as desired. For example, with whole blood, blood cells are separated from plasma. With the shown rotor 10, the cell-poor plasma, which is the desired complex fluid component to capture, is easily retrieved from its respective chamber 20 through a common inlet/outlet opening 22 provided in the housing of the rotor.

Figure 2:
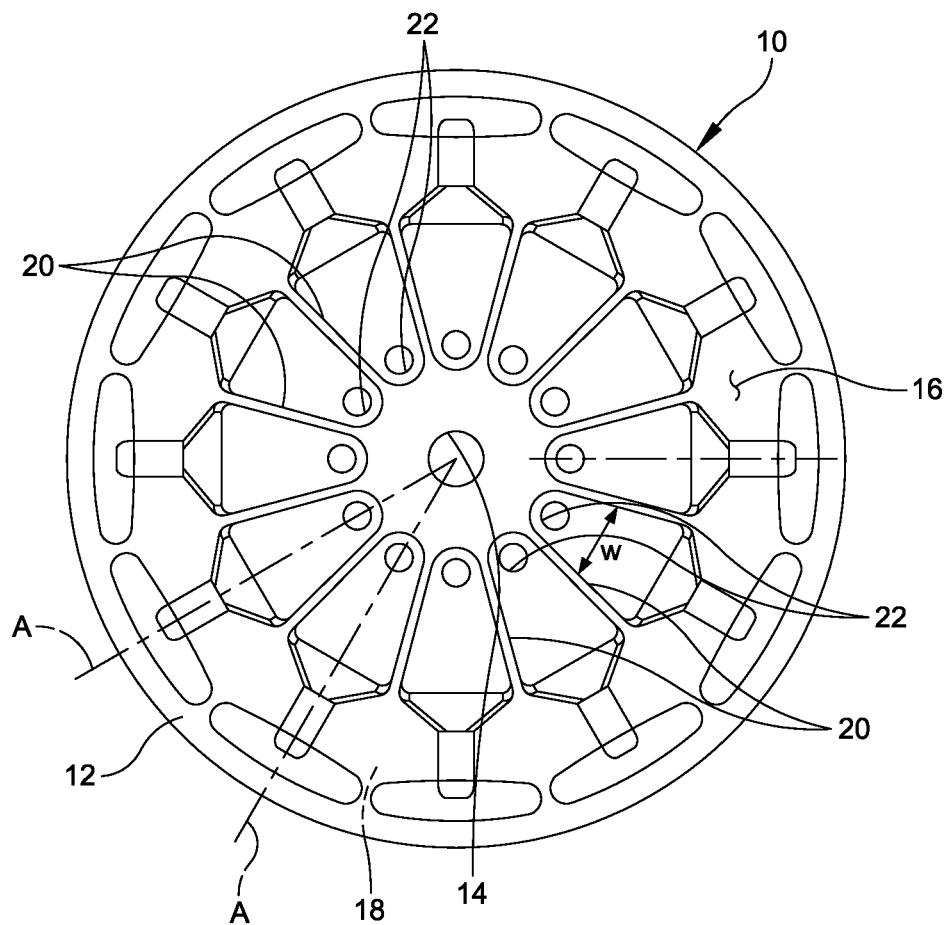
FIG. 2 is a top plan view of the rotor.
Figure 3A:
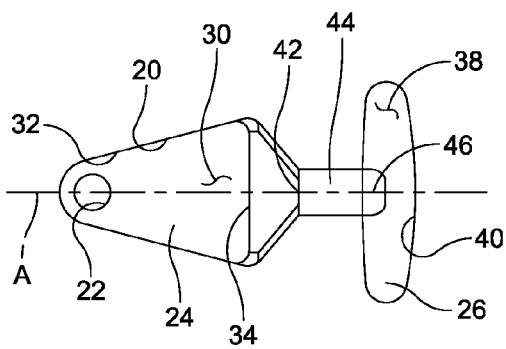
FIG. 3A is a schematic top view of a chamber of the rotor of one embodiment of the disclosure.
Figure 3B:
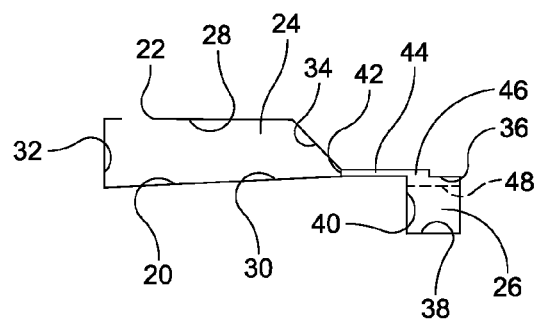
FIG. 3B is a schematic side view of the chamber shown in FIG. 3A.

Referring to FIG. 2 and to FIGS. 3A and 3B, each chamber 20 extends along a respective radial axis A extending from the central opening 14 to the periphery of the housing 12. In the shown embodiment, the chambers 20 are symmetrically arranged radially from and around the central opening 14 to help ensure balance of the rotor 10 during a centrifuge operation. The number of chambers (e.g., twelve) selected may be based on the number of samples being processed so long as the rotor is balanced during operation. Each chamber 20 includes a top wall (not designated) by the top half 16 of the housing 12, a bottom wall (not designated) formed by the bottom half 18 of the housing, and side walls (not designated) formed by the interface within the top half, the bottom half, or both halves. The inlet/outlet opening 22 is formed in the top wall of each chamber 20. The inlet/outlet opening 22 enables the insertion of complex fluid into the chamber and the extraction of a complex fluid component from the chamber. As will be discussed in greater detail below, the complex fluid may be inserted into the chamber 20 without forming a seal between a device, such as a pipette, containing the complex fluid and the housing 12 of the rotor 10. In addition, in one embodiment, the width and height of the first chamber portion 24 is larger than a capillary lengthscale of material in the vicinity of the inlet/outlet opening 22.

As best shown in FIGS. 3A and 3B, each chamber 20 includes two primary portions, a first chamber portion 24 having the inlet/outlet opening 22 and a second chamber portion 26 in fluid communication with the first chamber portion. The first chamber portion 24 includes a top wall portion 28, a bottom wall portion 30, a first side wall portion 32 and a second side wall portion 34. Similarly, the second chamber portion 26 includes a top wall portion 36, a bottom wall portion 38, and a side wall portion 40. The bottom wall portion 30 and the second side wall portion 34 of the first chamber portion 24 together create an outlet port 42 that communicates with an elongate channel 44 connecting the first chamber portion to an inlet port 46 provided in the top wall portion 36 of the second chamber portion 26.

As shown in FIG. 3B, the channel 44 has a small cross sectional area that restricts the free flow of fluid from the first chamber portion 24 to the second chamber portion 26. In one embodiment, the second chamber portion 26 is disposed generally below the first chamber portion 24. In addition, the second chamber portion 26 has a theoretical fill line 48 disposed generally below the inlet port 46 of the second chamber portion, the outlet port 42 of the first chamber portion 24, or both. The theoretical fill line represents a volume created by the second chamber portion 26 in which material is retained within the second chamber portion below the inlet port 46, the outlet port 42, or both. The configuration of the chamber 20 is such that when a centrifuge operation takes place, a first complex fluid component is retained within the first chamber portion 24 and a second complex fluid component is retained within the second chamber portion 26. With whole blood, most plasma is retained in the first chamber portion 24 and most blood cells are retained within the second chamber portion 26. Since the theoretical fill line 48 is below at least one of the inlet port 46 of the second chamber portion 26 and below the outlet port 42 of the first chamber portion 24, the second complex fluid component contained within the second chamber portion (e.g., blood cells) is retained in the second chamber portion.

Thus, when extracting the plasma from the first chamber portion 24, since the blood cells are separately retained within the second chamber portion 26, there is little or no risk of blood cells being extracted with the plasma or otherwise infiltrating the plasma. Plasma may be extracted from the first chamber portion 24 by the inlet/outlet opening 22 provided in the first chamber portion. In addition to configuring the fill line 48 of the second chamber portion 26 below the inlet port 46 of the second chamber portion (and the outlet port 42 of the first chamber portion 24), the elongated, narrow channel 44 provides a bather between the first and second chamber portions 24, 26 to minimize possible mixing of the separated fluids. Specifically, during the process of centrifugation, cells are separated from plasma and retained in the second chamber portion 26, while the non-cellular components of the whole blood (mainly plasma) are retained in the first chamber portion and possibly the channel 44. During removal of the plasma from the first chamber portion 24, most plasma is extracted through the inlet/outlet opening 22; however, some plasma is retained in the channel 44 primarily due to the surface tension of the plasma material in the channel. Thus, in this embodiment, the small cross section of the channel 44 is to minimize waste of plasma when extracting the plasma. Moreover, the second chamber portion 26 has a capacity greater than an amount of the second complex fluid component (e.g., blood cells) retained in the second chamber portion 26. This reduces the risk of spillage of the second complex fluid component back into the first chamber portion 24 and provides robustness against the fluid composition, such as blood that may have a range of hematacrit or packed cell volume.

As best shown in FIGS. 2 and 3A, the first chamber portion 24 is disposed inboard with respect to the second chamber portion 26 along axis A, with the inlet/outlet opening 22 being disposed toward the center of the rotor 10. The first chamber portion 24 has a width that is wider than the channel 44 and a height substantially greater than a height of the channel. Although a channel, such as channel 44, is provided, it should be noted that the channel may be eliminated as shown in other chamber embodiments discussed herein. The volume of the first chamber portion 24 is sufficient to retain the entire sample being deposited into the chamber 20 through the inlet/outlet opening 22. Specifically, referring to FIG. 3B, the first chamber portion 24 has a height and a depth so that the complex fluid deposited into the first chamber portion through the inlet/outlet opening 22 is substantially retained within the first chamber portion prior to performing a centrifuge operation.

In a certain embodiment, the bottom wall portion 30 of the first chamber portion 24 slopes upwardly to the outlet port 42 so that the first complex fluid component captured within the first chamber portion, such as plasma after a centrifuge operation, is more easily accessed and withdrawn through the inlet/outlet opening 22. Specifically, the sloped bottom wall portion 30 increases the recovery rate of the plasma thus minimizing plasma waste during extraction. As shown, the inlet/outlet opening 22 is positioned on the rotor so that the opening is disposed above where the first complex fluid, when deposited within the first chamber portion 24, component pools within the first chamber portion for enhancing the extracting of the fluid component from the first chamber portion.

In the shown embodiment, the channel 44 has a height and a width that are substantially smaller than a height and a width of the first channel portion 24. The second chamber portion 26 is disposed below the inlet port 46 of the second chamber portion, the outlet port 42 of the first chamber portion 24, or both, and includes a height and a width configured to retain the second complex fluid component within the second chamber portion after a centrifuge operation. The second side wall 34 of the first chamber portion 24 slopes toward the outlet port 42 of the first chamber portion 24 so as to assist in delivering the initial complex sample (e.g., a biological fluid, such as whole blood) or components thereof to the outlet port 42 and to reduce damage to said components (e.g., RBC lysis). Additionally, the second side wall 34 is angled in order to minimize the possibility of trapping air bubbles inside the first chamber portion 24 during the sample filling process. Trapped air within the first chamber portion 24 may jeopardize the successful filling of the first chamber portion, provided the first chamber portion is not significantly larger than the intended volume of the initial sample to be loaded into the first chamber portion. The angled second side wall 34 coupled with the narrow configuration of the outlet port 42 assist in capturing fluid within the first chamber portion 24. Additionally, by configuring the second side wall 34 to be at an angle, cells that reach this side wall can travel down the wall to the outlet port 42.

It should be understood that the chambers 20 of the rotor 10 may be constructed in many other ways, and that other chamber configurations may be provided and fall within the scope of the present disclosure. For example, in FIGS. 4A and 4B, a chamber 50 of another embodiment is provided having a first chamber portion 52 that is stepped along a z-axis above a second chamber portion 54 with a sloped channel 56 providing fluid communication between the first and second chamber portions. An outlet port 58 of the first chamber portion 52 and an inlet port 60 of the second chamber portion 54 are both disposed above a fill line 62 of the second chamber portion.

Figure 5A:
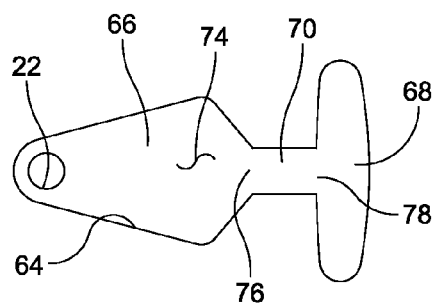
FIG. 5A is a schematic top view of a chamber of the rotor of another embodiment of the disclosure.
Figure 5B:
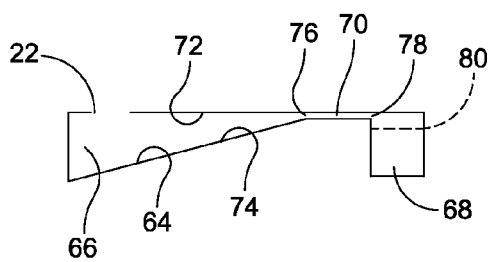
FIG. 5B is a schematic side view of the chamber shown in FIG. 5A.

In FIGS. 5A and 5B, a chamber 64 of another embodiment is provided having a first chamber portion 66, a second chamber portion 68 and a channel 70 connecting the first chamber portion to the second chamber portion. The channel 70 is disposed above the first chamber portion 66 and the second chamber portion 68 along a z-axis. As shown, a top wall 72 of the chamber 64 is straight, and a bottom wall 74 of the chamber forms the bottom wall portions of the first and second chamber portions 66, 68 and the channel 70. An outlet port 76 of the first chamber portion 66 and an inlet port 78 of the second chamber portion 68 are both disposed above a fill line 80 of the second chamber portion.

Figure 6A:
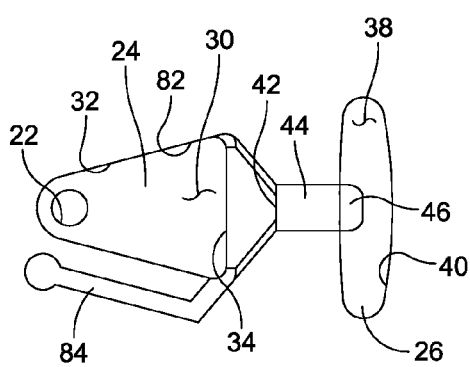
FIG. 6A is a schematic top view of a chamber of the rotor of another embodiment of the disclosure.
Figure 6B:
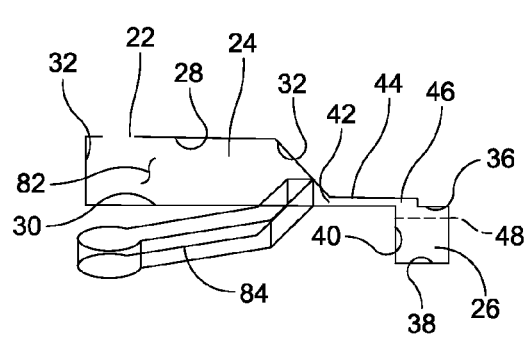
FIG. 6B is a schematic side and partial perspective view of the chamber shown in FIG. 6A.

In FIGS. 6A and 6B, a chamber 82 of another embodiment is provided that is similar to chamber 20 in that it includes a first chamber portion 24, a second chamber portion 26 and a channel 44 providing fluid communication between the first and second chamber portions. The difference between chamber 82 and chamber 20 is the provision of a separate outlet channel 84 that is used to extract the first complex fluid component from the first chamber portion 24 after a centrifuge operation takes place. At least a portion of the outlet channel 84 may be disposed generally below the first chamber portion 24 in such a position that a collection point at an end of the outlet channel is positioned below the bottom of the first chamber portion. The outlet channel 84 may further include an outlet port to remove fluid from the outlet channel. In addition, an outlet port 42 of the first chamber portion 24 and an inlet port 46 of the second chamber portion 26 are both disposed above a fill line 48 of the second chamber portion. While the bottom wall portion 30 of the first chamber portion 24 may be level (as shown), this bottom wall portion may be angled to direct fluid towards the outlet channel 84 during withdrawal of the first complex fluid type (e.g., plasma). Additionally, the outlet channel 84 may be designed to be of shape, size, material, or surface character so as to prevent the outlet channel 84 from filling during the initial loading stage of the sample, as to prevent the outlet channel 84 from filling during the initial loading stage of the sample. This design, enabling air to flow behind the fluid rather than over the fluid during withdrawal, may have particular advantages when working with small dimensions, such as dimensions which are similar to or smaller than the capillary length of the fluid.

Figure 4A:
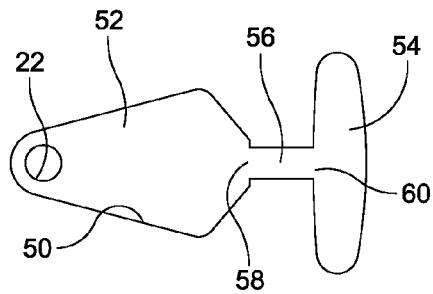
FIG. 4A is a schematic top view of a chamber of the rotor of another embodiment of the disclosure.
Figure 4B:
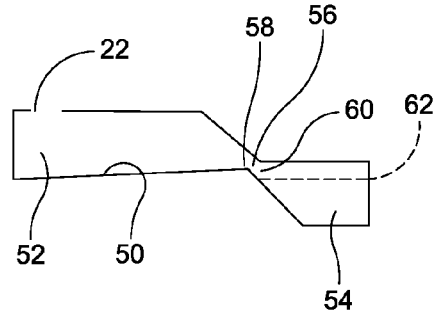
FIG. 4B is a schematic side view of the chamber shown in FIG. 4A.
Figure 7A:
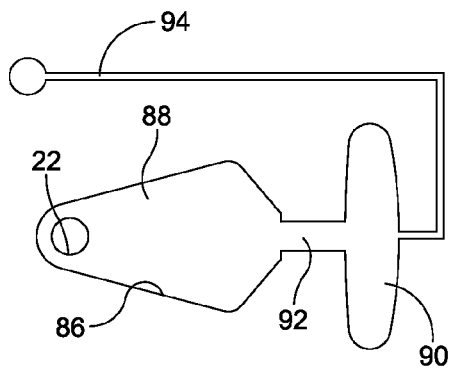
FIG. 7A is a schematic top view of a chamber of the rotor of another embodiment of the disclosure.
Figure 7B:
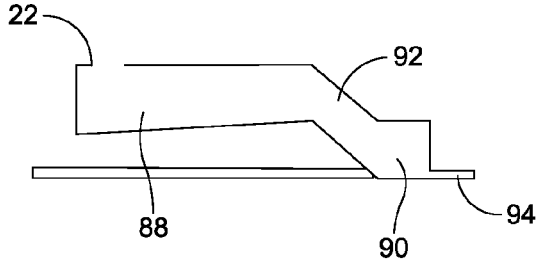
FIG. 7B is a schematic side view of the chamber shown in FIG. 7A.

In FIGS. 7A and 7B, a chamber 86 of another embodiment is provided having a first chamber portion 88, a second chamber portion 90 and a sloped channel 92 that is similar in construction to the chamber 50 shown and described with reference to FIGS. 4A and 4B. The primary difference is that a vent channel 94 is provided in fluid communication with the second chamber portion 90 to reduce the risk of air being trapped within the chamber 86 during loading of the sample. The provision of the vent channel 94 capable of exhausting trapped air from the chamber 86 serves an important function when a dimension of the chamber is small, such as of order or smaller than the capillary lengthscale. The vent channel 94 may also make withdrawal of fluids much easier in some such cases.

Figure 8A:
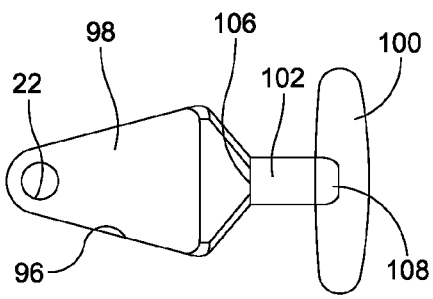
FIG. 8A is a schematic top view of a chamber of the rotor of another embodiment of the disclosure.
Figure 8B:
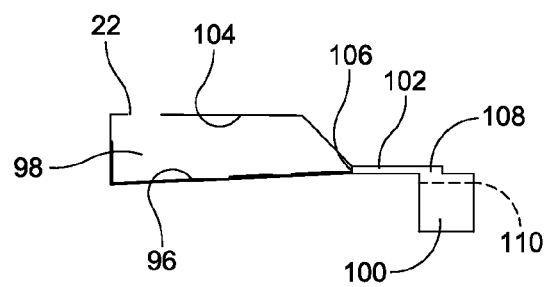
FIG. 8B is a schematic side view of the chamber shown in FIG. 8A.

In FIGS. 8A and 8B, a chamber 96 of another embodiment is provided having a first chamber portion 98, a second chamber portion 100 and a channel 102 connecting the first chamber portion to the second chamber portion. The channel 102 is disposed above a portion of the first chamber portion 98 and the entire second chamber portion 100 along a z-axis. The chamber 96 is similarly constructed as the chamber 64 with reference to FIGS. 5A and 5B in that the chamber 96 is a hybrid between chamber 64 and the chamber 20. As shown, the first chamber portion 98 has a chamber volume that is much larger than a volume of a sample being received by the chamber 96. Thus, this design enables the disposition of a complex fluid into the first chamber portion 98 without a seal between a device (e.g., a pipette) handling the fluid and the opening 22 of the chamber 96. Additionally, a top wall 104 of the first chamber portion 98, although having a sloped top wall, does not require the sloped top wall since the first chamber portion has a sufficient capacity to receive the entire sample. However, the sloped top wall of the first chamber portion 98 may be angled as shown in order to achieve several functions.

For example, the sloped bottom wall of the first chamber portion 98 can direct liquid towards the inlet/outlet opening 22 to increase yield of liquid recovery. The slope of the bottom wall, in conjunction with the slope of the top wall, can also reduce the first component of the complex fluid from being trapped in the corners of the first chamber portion 98 and increase fluid recovery. Moreover, this construction reduces residual liquid trapped between the top and the bottom wall of the first chamber portion 98 near the opening 22 of the first chamber portion, which also helps increase the yield of liquid recovery. Normally, after a centrifugation process, the first component of the complex fluid tends to be trapped in the narrow corners of the first chamber portion 98 because of surface tension. This also helps increase the yield of liquid recovery while minimizing the possibility of trapping air bubbles inside the first chamber portion 98 during the sample filling process. With chambers having a smaller volume, the sloped top wall enables the first chamber portion to be filled without forming a seal between the device (e.g., a pipette) and the rotor. An outlet port 106 of the first chamber portion 98 and an inlet port 108 of the second chamber portion 100 are both disposed above a fill line 110 of the second chamber portion.

Figure 9A:
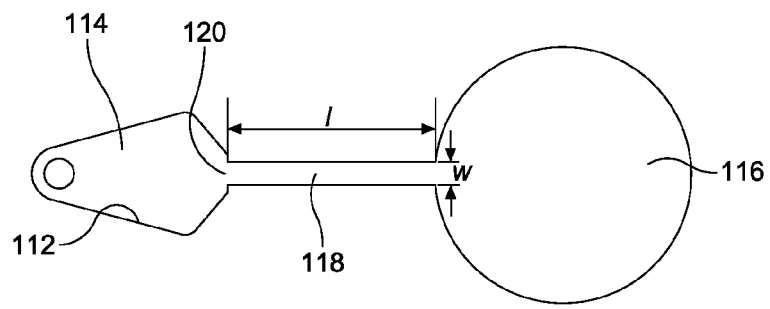
FIG. 9A is a schematic top view of a chamber of the rotor of another embodiment of the disclosure.
Figure 9B:
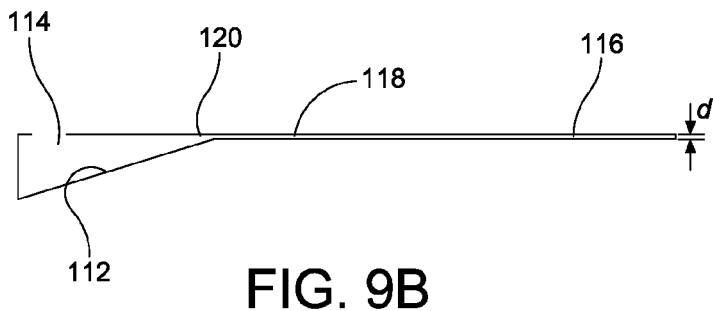
FIG. 9B is a schematic side view of the chamber shown in FIG. 9A.

In FIGS. 9A and 9B, a chamber 112 of another embodiment is provided having a first chamber portion 114, a second chamber portion 116 and an elongate, narrow channel 118 connecting the first chamber portion to the second chamber portion. As shown, the first chamber portion 114 is configured similarly to the first chamber portion 66 of chamber 64 shown and described with reference to FIGS. 5A and 5B. The second chamber portion 116 is disposed along the same plane as an outlet port 120 of the first chamber portion 114 and the channel 118. The channel 118 is configured so that when a centrifuge operation takes place, a first complex fluid component is retained in the first chamber portion 114 and a second complex fluid component is retained in the second chamber portion 116. Specifically, the channel 118 has a sufficient length (l) and a narrow cross-sectional area (width (w) by depth (d)) to ensure that the second complex fluid component received and captured within the second chamber portion 116 does not migrate or re-mix with the first complex fluid component captured within the first chamber 114 after a centrifuge operation takes place.

Figure 10A:
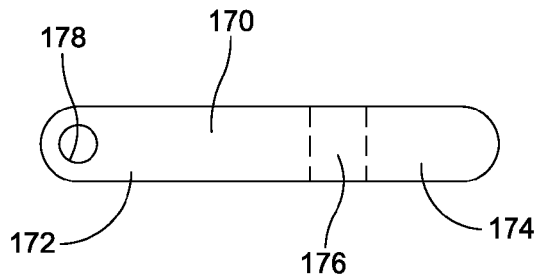
FIG. 10A is a schematic top view of a chamber of the rotor of another embodiment of the disclosure.
Figure 10B:
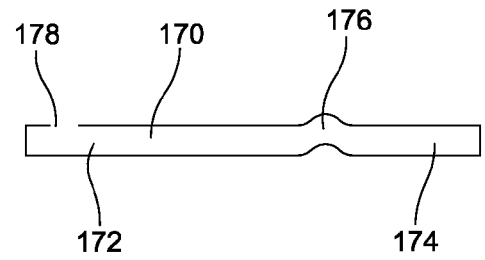
FIG. 10B is a schematic side view of the chamber shown in FIG. 10A.

In FIGS. 10A and 10B, a chamber 170 of another embodiment is provided having a first chamber portion 172, a second chamber portion 174 and a "channel" 176 connecting the first chamber portion to the second chamber portion. The channel 176 is disposed above the first chamber portion 172 and the second chamber portion 174 along a z-axis. An inlet/outlet opening 178 is provided in the first chamber portion 172. The channel 176 is configured to separate a first complex fluid component substantially retained in the first chamber portion 172 (e.g., plasma) from a second complex fluid component substantially retained in the second chamber portion 174 (e.g., blood cells).

Figure 11A:
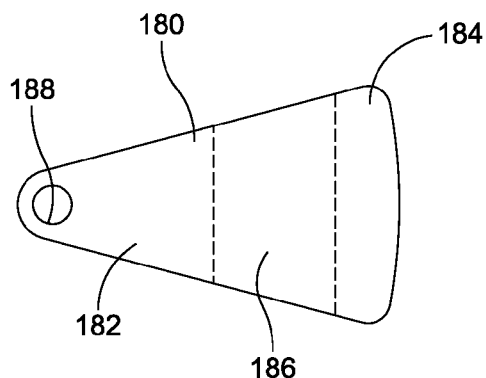
FIG. 11A is a schematic top view of a chamber of the rotor of another embodiment of the disclosure.
Figure 11B:
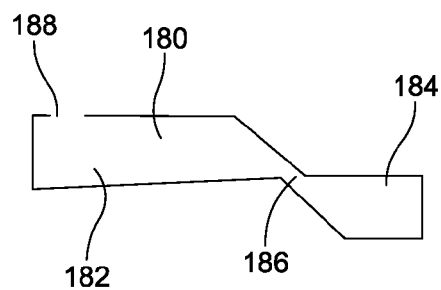
FIG. 11B is a schematic side view of the chamber shown in FIG. 11A.

In FIGS. 11A and 11B, a chamber 180 of another embodiment is provided having a first chamber portion 182, a second chamber portion 184 and a sloped channel 186. As shown in FIG. 11A, the first chamber portion 182 is wedge-shaped. An inlet/outlet opening 188 is provided in the first chamber portion 182.

Figure 12A:
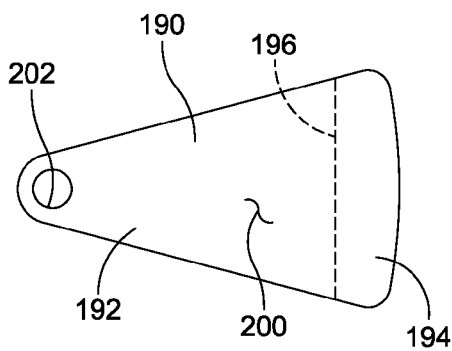
FIG. 12A is a schematic top view of a chamber of the rotor of another embodiment of the disclosure.
Figure 12B:
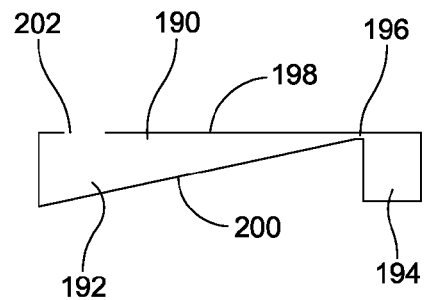
FIG. 12B is a schematic side view of the chamber shown in FIG. 12A.

In FIGS. 12A and 12B, a chamber 190 of another embodiment is provided having a first chamber portion 192, a second chamber portion 194 and a constricted area 196 connecting the first chamber portion to the second chamber portion. The constricted area 196 is disposed above the first chamber portion 192 and the second chamber portion 194 along a z-axis. As shown, a top wall 198 of the chamber 190 is straight, and a bottom wall 200 of the chamber forms the bottom wall portions of the first and second chamber portions 192, 194 and the channel 196. As shown in FIG. 12A, the first chamber portion 192 is wedge-shaped. An inlet/outlet opening 202 is provided in the first chamber portion 192.

Figure 13A:
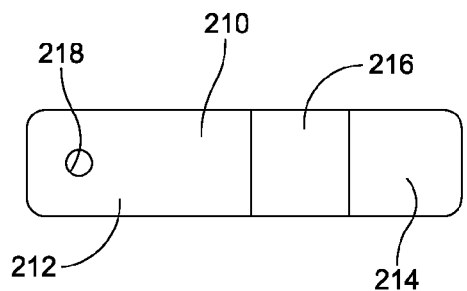
FIG. 13A is a schematic top view of a chamber of the rotor of another embodiment of the disclosure.
Figure 13B:
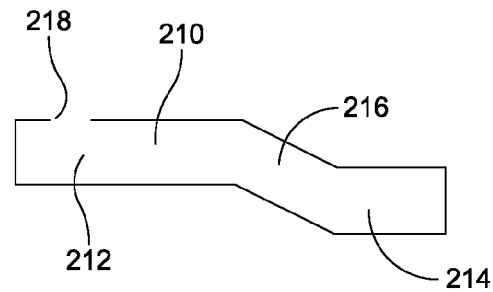
FIG. 13B is a schematic side view of the chamber shown in FIG. 13A.

In FIGS. 13A and 13B, a chamber 210 of another embodiment is provided having a first chamber portion 212, a second chamber portion 214 and a sloped channel 216. As shown in FIG. 13A, the first chamber portion 182 is rectangular-shaped. An inlet/outlet opening 218 is provided in the first chamber portion 212.

It should be understood that the construction of the bottom and the side walls of a chamber may vary, with the walls leading into and out of the channel controlling the flow of fluid between respective portions of the chamber.

Figure 14A:
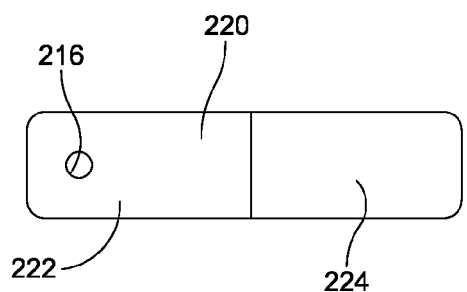
FIG. 14A is a schematic top view of a chamber of the rotor of another embodiment of the disclosure.
Figure 14B:
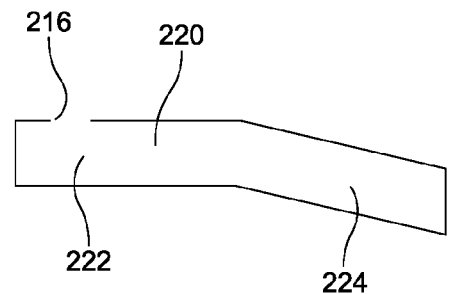
FIG. 14B is a schematic side view of the chamber shown in FIG. 14A.

In FIGS. 14A and 14B, a chamber 220 of another embodiment is provided having a first chamber portion 222 and a second chamber portion 224. As shown in FIG. 14A, the first chamber portion 182 is rectangular-shaped. As shown in FIG. 14B, the first chamber portion 222 transitions directly to the second chamber portion 224, with the second chamber portion angled downwardly with respect to the first chamber portion. An inlet/outlet opening 216 is provided in the first chamber portion 222.

Figure 15A:
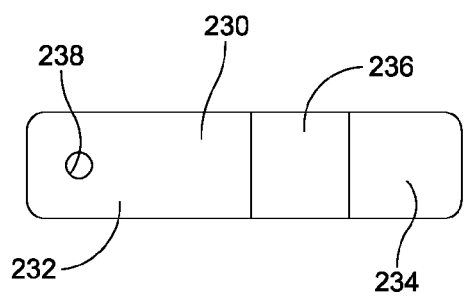
FIG. 15A is a schematic top view of a chamber of the rotor of another embodiment of the disclosure.
Figure 15B:
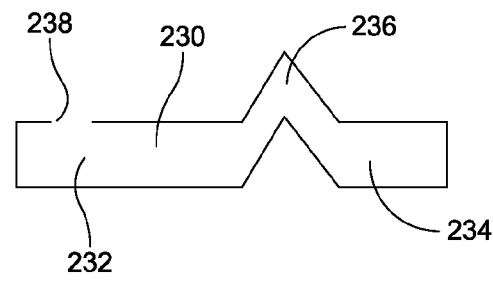
FIG. 15B is a schematic side view of the chamber shown in FIG. 15A.

In FIGS. 15A and 15B, a chamber 230 of another embodiment is provided having a first chamber portion 232, a second chamber portion 234 and a "channel" 236 connecting the first chamber portion to the second chamber portion. The channel 236 is disposed above the first chamber portion 232 and the second chamber portion 234 along a z-axis. An inlet/outlet opening 238 is provided in the first chamber portion 232. The channel 236 is configured to separate a first complex fluid component substantially retained in the first chamber portion 232 (e.g., plasma) from a second complex fluid component substantially retained in the second chamber portion 234 (e.g., blood cells). As compared with the channel 176 of chamber 170 illustrated in FIGS. 10A and 10B, the channel 236 is move of an inverted "V" shape rather than a curved inverted "U" shape, and the highest point of a lower surface in the channel 236 is near, equal, or higher than a height of an upper surface of the second chamber portion 234.

Figure 16:
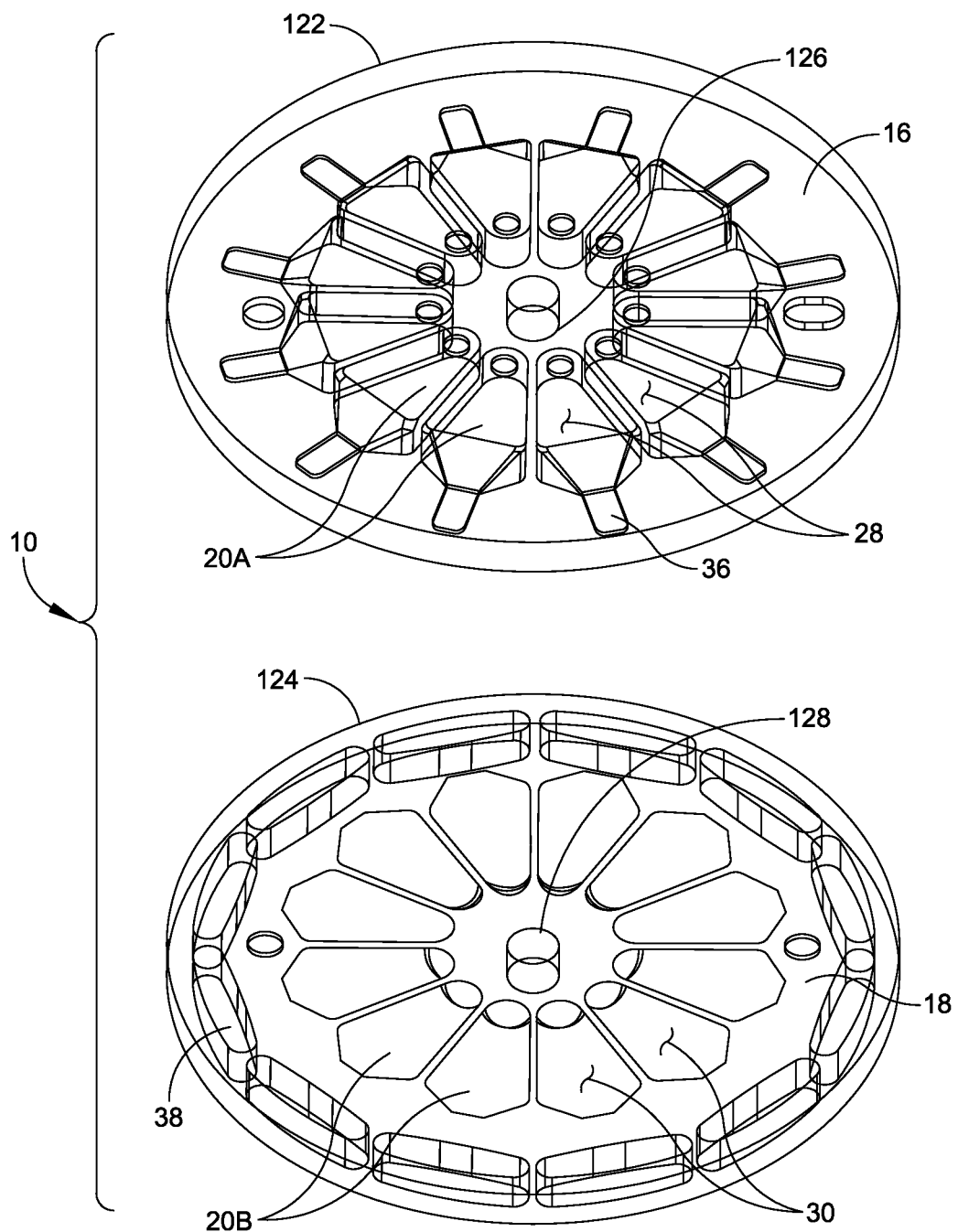
FIG. 16 is an exploded perspective view of top and bottom rotor halves in spaced relation to one another.

Referring to FIG. 16, the construction of the rotor 10 will now be described. As shown, the housing 12 of the rotor 10 includes the top half 16 and the bottom half 18, which combine to form the chambers 20 of the rotor, represented by 20A associated with the top half and 20B associated with the bottom half. As described above, the top and bottom halves 16, 18 of the housing 12 may be secured to one another at contact points, including their respective peripheries 122, 124. Additionally, the halves 16, 18 are joined to one another at 126, 128 at the location of the central opening 22 of the rotor 10 and around the individual chambers 20. Prior to being joined, the top and bottom halves 16, 18 are aligned so that the top wall portions 28, 36 and the bottom wall portions 30, 38 of each chamber 20 are aligned prior to being secured to one another. In one embodiment, the top and bottom halves 16, 18 of the housing 12 are secured to one another by ultrasonic welding, laser welding, or some other technique suitable for joining plastic. The arrangement is such that each chamber 20 is suitably sealed so that sample complex fluids deposited within the chamber remain within the chamber. The top half 16 and the bottom half 18 of the housing 12 may be fabricated from any suitable material, such as plastic. The housing 12 may be see-through or transparent or translucent so that an operator of the centrifuge system may visually identify the samples being process by the rotor 10.

Figure 17:
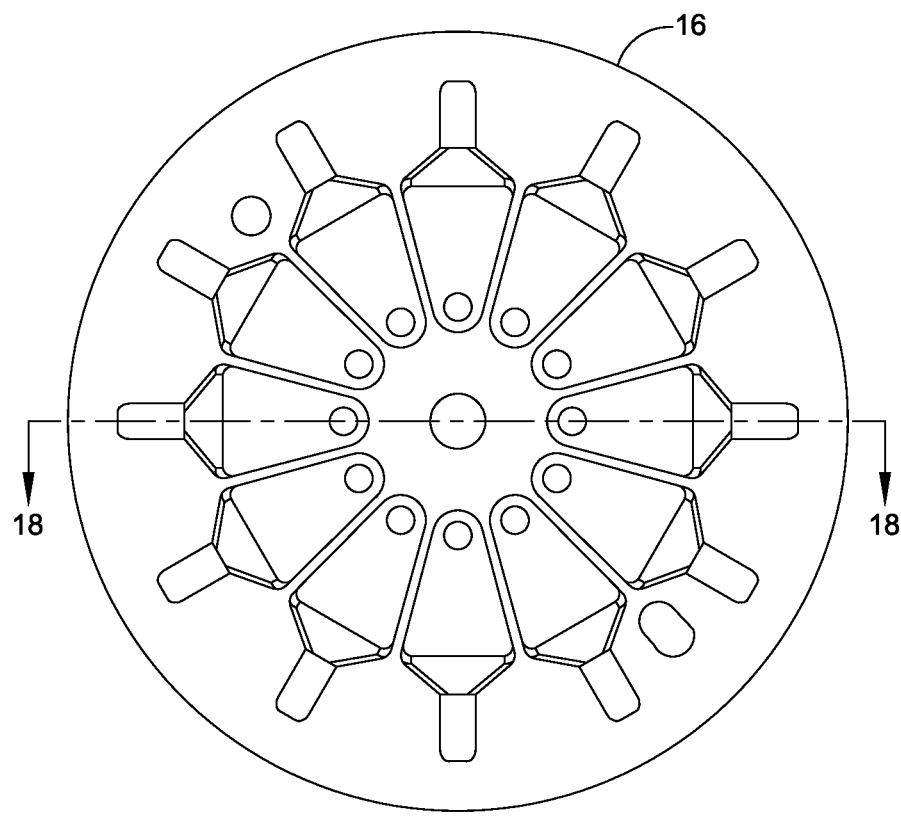
FIG. 17 is a top plan view of the top rotor half shown in FIG. 16.
Figure 18:
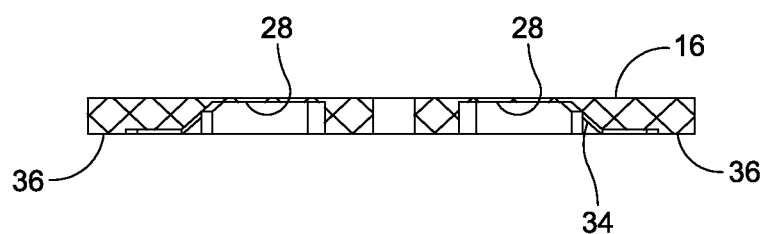
FIG. 18 is a cross-sectional view taken along line 18-18 in FIG. 17.

FIG. 17 illustrates a top plan view of the top half of the housing 12. As shown with additional reference to FIGS. 3A and 3B, in one embodiment, the channel 44 may have a width of 6.1 millimeters and a length of 11.8 millimeters. The inlet/outlet opening 22 may have a diameter of 5.0 millimeters. FIG. 18 shows a cross-sectional view of the top half 16 taken along line A-A in FIG. 17, which shows the top half 16 defining the top wall portions 28, 36 of the first and second chamber portions 24, 26, respectively, which are illustrated in FIGS. 3A and 3B. As shown, in one embodiment, the slope or angle of the second side wall portion 34 is approximately 45 degrees.

Figure 19:
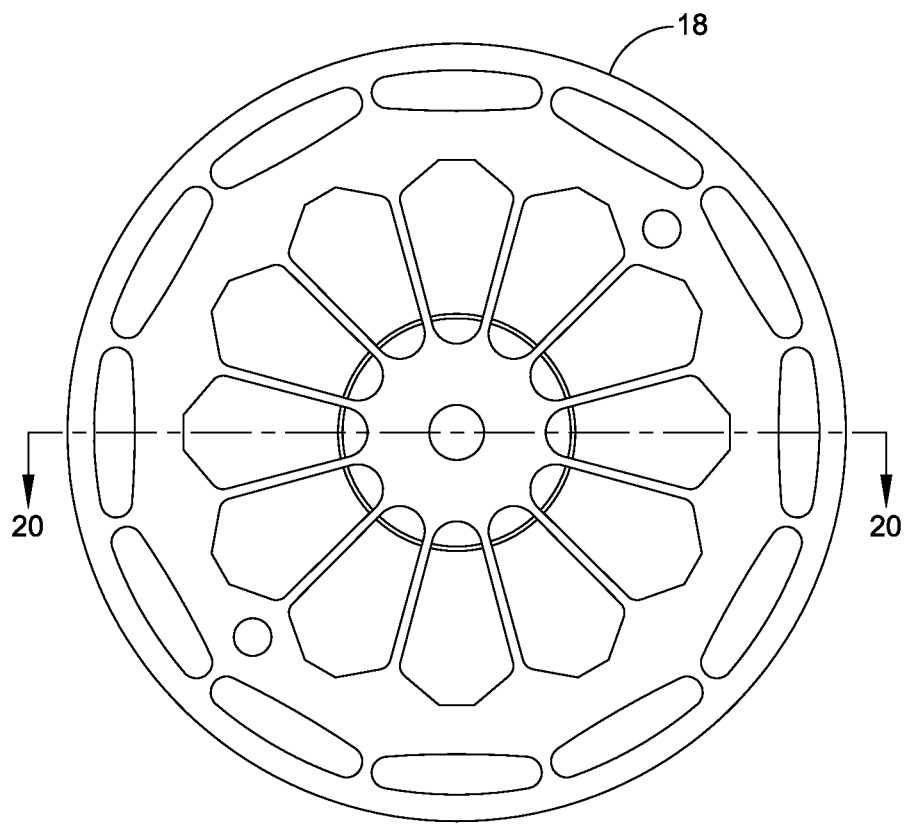
FIG. 19 is a top plan view of the bottom rotor half shown in FIG. 16.
Figure 20:
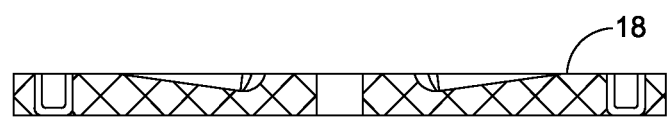
FIG. 20 is a cross-sectional view taken along line 20-20 in FIG. 19.

FIG. 19 illustrates a top plan view of the bottom half 18 of the housing 12 shown in FIG. 1. As shown, with additional reference to FIGS. 3A and 3B, in one embodiment, the rotor 10 has a diameter of 135.2 millimeters. Each chamber 20 is radially spaced at 30 degree intervals from each other. FIG. 20 shows a cross-sectional view of the bottom half 18 taken along line A-A in FIG. 19, which shows the bottom wall portions 30, 38 of the first and second chamber portions 24, 26, respectively. As shown, the top half 16 and the bottom half 18 illustrated in FIGS. 17-20 create the chambers 20. It should be understood that a person skilled in the art, provided the benefit of the present disclosure, may configure the top half 16 and the bottom half 18 to create the chambers 50, 64, 82, 86, 96 and 112 illustrated in FIGS. 4A and 4B, 5A and 5B, 6A and 6B, 7A and 7B, 8A and 8B, and 9A and 9B, respectively, for example.

Turning now to FIGS. 21-23, the sequence of operation of the rotor 10 when loading as sample into the rotor, performing a centrifuge operation on the rotor, and withdrawing a first complex fluid component from the rotor will be described. As described herein, the complex fluid may be a biological fluid, such as whole blood. FIG. 21A illustrates a device, such as a pipette 130, used to fill the chamber 20 of the rotor 10. As shown, the pipette 130 is inserted into the inlet/outlet opening 22 with or preferably without sealing the interface between the pipette and the top wall forming the inlet/outlet opening. FIGS. 21B, 21C and 21D illustrate the first chamber portion 24 being filled with a biological fluid, such as whole blood. As shown in FIG. 21D, the biological fluid is retained in the first chamber portion 24 by virtue of the narrow constriction between the outlet port of the first chamber portion and the channel 44. The fluid characteristics maintain the biological fluid in the first chamber portion 24, although seepage of fluid to the second chamber portion 26 is acceptable or in some cases may be desirable.

FIG. 22A illustrates the chamber 20 prior to performing a centrifuge operation, i.e., spinning the rotor at high revolutions per minute (RPM). For example, the rotor 10 may be rotated for 45 seconds at 10,500 RPMs. In FIG. 22B, the biological fluid moves into the second chamber portion 26 by virtue of centrifugal force being applied to the biological fluid. Generally, the force will overcome the surface tension destabilizing the interface, allowing fluid to flow into the second chamber portion 26 and air to escape from the second chamber portion 26 into the first chamber portion 24. In FIG. 22C, the biological fluid is being separated into a first complex fluid component that is retained in the first chamber portion 24 and a second complex fluid component that is retained in the second chamber portion 26. FIG. 22D illustrates the biological fluid in the chamber 20 at the end of the centrifuge operation.

FIGS. 23A-23D illustrate the relaxation of the biological fluid and the removal of the first complex fluid component (e.g., plasma) from the first chamber portion 24. FIGS. 23A and 23B illustrate the relaxation of the first complex fluid component. FIG. 23C illustrates a pipette 130 being inserted into the inlet/outlet opening 22 of the chamber 20. FIG. 23D illustrates the removal of the first complex fluid component from the first chamber portion 24. As shown, the first complex fluid component can be removed from the first chamber portion 24 without drawing the second complex fluid component (e.g., blood cells) from the second chamber portion 26.

The operation of the rotor on a centrifuge system, as illustrated in FIGS. 21-23, may be performed on rotors having other chamber designs and still fall within the scope of the present disclosure. For example, the rotor may include the chamber designs illustrated in FIGS. 4A and 4B, 5A and 5B, 6A and 6B, 7A and 7B, 8A and 8B, and 9A and 9B, as well as the chamber designs described below.

Figure 24:
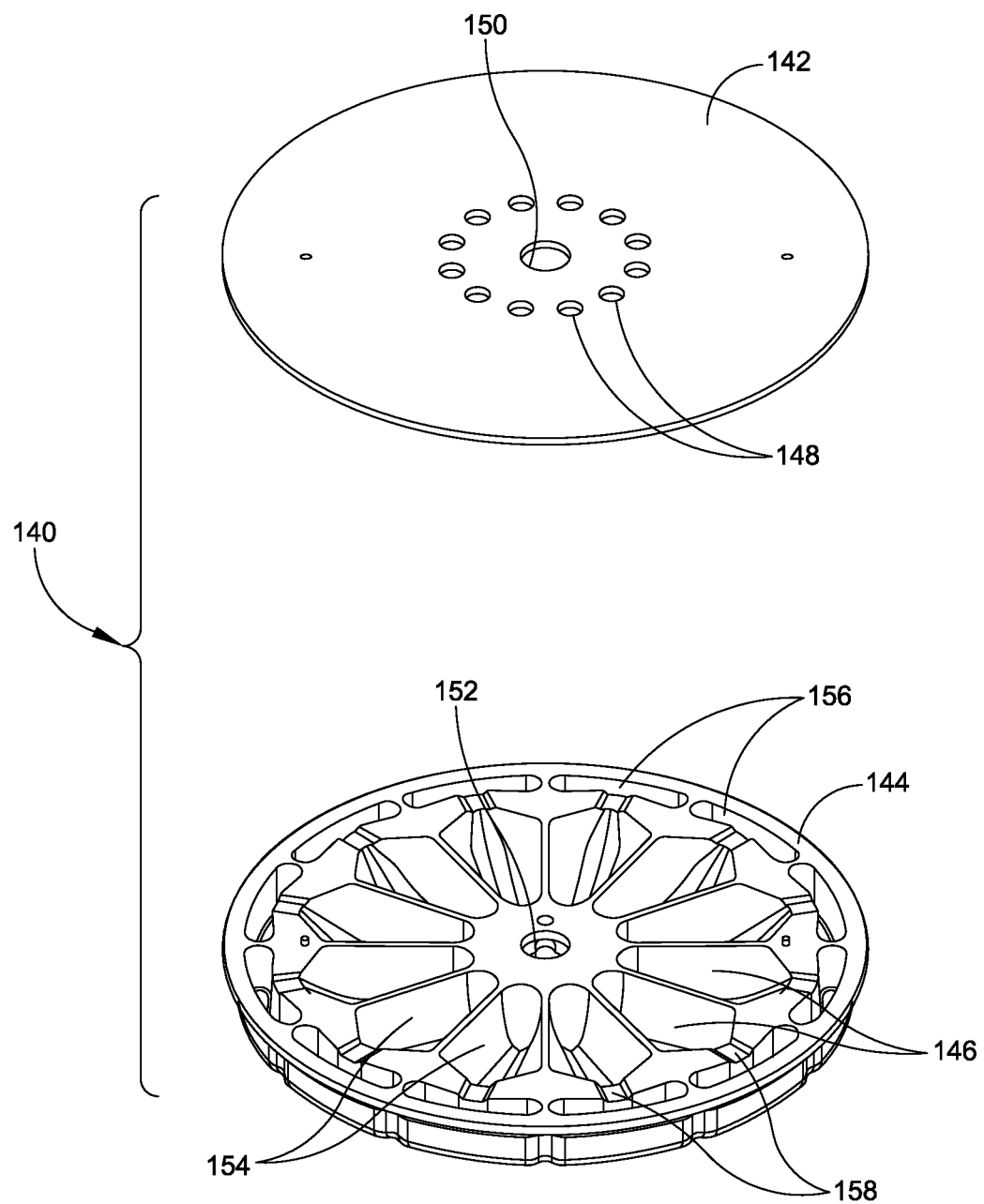
FIG. 24 is an exploded perspective view of a rotor of another embodiment of the disclosure.
Figure 25:
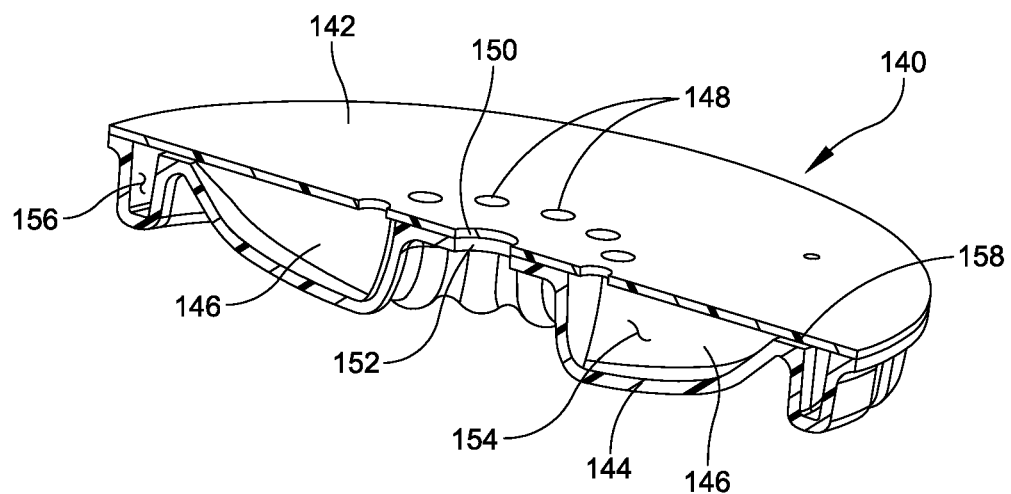
FIG. 25 is a cross-sectional perspective view of the rotor shown in FIG. 24.

FIGS. 24 and 25 illustrate a rotor, generally indicated at 140, of another embodiment of the disclosure. As shown, the rotor 140 includes a planar top half 142 and a bottom half 144 that are secured to one another at every location in which the top half contacts the bottom half. The top half 142 and the bottom half 144 may be fabricated from any suitable material, such as plastic. As with rotor 10, the rotor 140 may be transparent or translucent so that an operator of the centrifuge system may visually identify or otherwise inspect the samples being processed by the rotor. In one embodiment, the top and bottom halves 142, 144 are secured to one another by ultrasonic welding, laser welding, or some other technique suitable for joining plastic.

Samples of complex fluids (e.g., biological fluids, such as whole blood) are received within one or more chambers, each generally indicated at 146, defined within the bottom half 144 of the rotor 140. In the shown embodiment, there are twelve chambers 146 provided in the rotor 140. When a centrifuge operation takes place, the complex fluids are separated as desired. For example, with whole blood, blood cells are separated from plasma. With the shown rotor 140, the plasma, which is the desired biological fluid to capture, is easily retrieved from its respective chamber 146 through a common inlet/outlet opening 148 provided in the top half 142 of the rotor.

As shown, the top half 142 has a central opening 150 and the bottom half 144 has a corresponding central opening 152. Each chamber 146 extends along a respective radial axis extending from the central opening 152 to the periphery of the bottom half 144. In the shown embodiment, the chambers 146 are symmetrically arranged radially from and around the central opening 152. Each chamber 146 includes a top wall defined by the top half 142 of the rotor 140. The inlet/outlet openings 148 enable the insertion of complex fluids into the chambers and the extraction of complex fluid components from the chambers. As will be discussed in greater detail below, the complex fluid may be inserted into each chamber 146 without forming a seal between a device, such as a pipette, containing the complex fluid and the top half 142 of the rotor 140. Prior to being joined, the top and bottom halves 142, 144 are aligned so that the inlet/outlet openings 148 and the chambers 146 are aligned prior to being secured to one another. The arrangement is such that each chamber 146 is suitably sealed so that sample complex fluids deposited within the chamber remain within the chamber.

Each chamber 146 includes two primary portions, a first chamber portion 154 and a second chamber portion 156 in fluid communication with the first chamber portion. A channel 158 connects the first chamber portion 154 to the second chamber portion 156 to provide fluid communication therebetween. For each chamber 146, the top half 142 of the rotor 140 defines a top wall portion of the first chamber portion 154, the second chamber portion 156 and the channel 158. The bottom half 144 defines a bottom wall portion and a side wall portion. Similarly, for the second chamber portion 156, the bottom half 144 includes a bottom wall portion and a side wall portion. The bottom wall portion and the side wall portion of the first chamber portion 154 together create an outlet port that communicates with the channel 158.

As with rotor 10, the channel 158 of rotor 140 has a small cross sectional area that restricts the free flow of fluid from the first chamber portion 154 to the second chamber portion 156. In one embodiment, the second chamber portion 156 is disposed generally below the first chamber portion 154. In addition, the second chamber portion 156 has a theoretical fill line disposed generally below the outlet port of the first chamber portion, an inlet port of the second chamber portion, or both. The theoretical fill line represents a volume created by the second chamber portion 156 in which material is retained within the second chamber portion below the inlet port, the outlet port, or both. The configuration of the chamber 146 is such that when a centrifuge operation takes place, a first complex fluid component is retained within the first chamber portion 154 and a second complex fluid component is retained within the second chamber portion 156.

Figure 26:
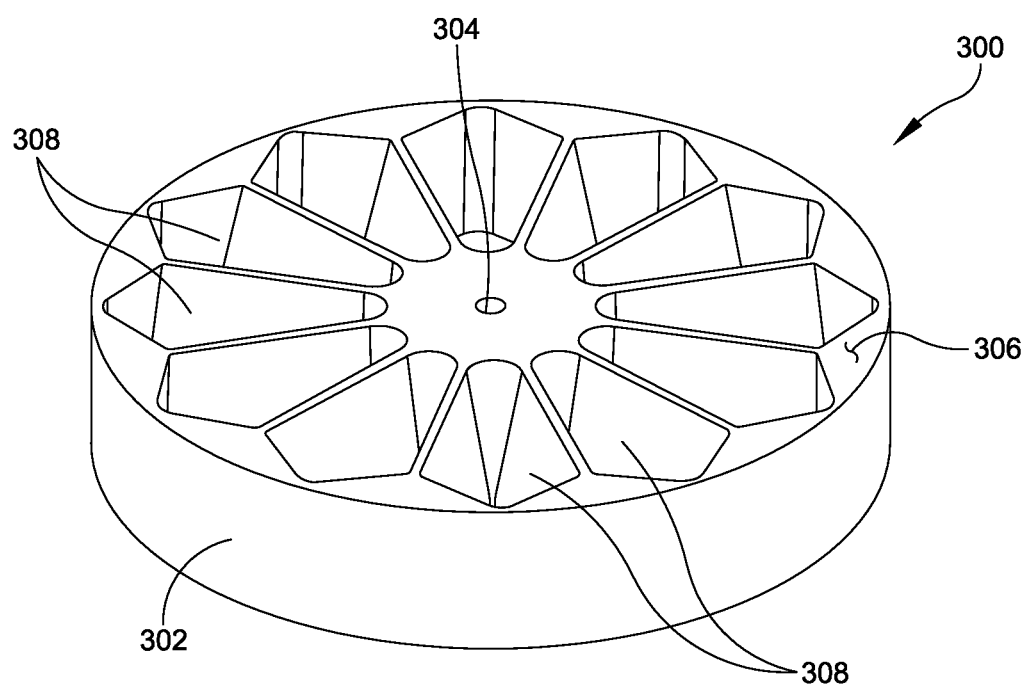
FIG. 26 is a perspective view of a rotor of another embodiment of the disclosure.

FIG. 26 illustrates a rotor, generally indicated at 300, of another embodiment of the present disclosure. As with the rotors described thus far, rotor 300 is configured to spin samples of biological fluids, such as whole blood, requiring separation. As shown, the rotor 300 includes a disc-shaped body or housing 302 having a central opening 304 formed therein that is configured to be secured to and spun on a centrifuge system. The housing 302 includes top surface 306 having a plurality of receptacles, each indicated at 308, formed therein, the purpose of which will become apparent as the description of the rotor 300 proceeds. The receptacles 308 are symmetrically arranged radially from and around the central opening 304 to help ensure balance of the rotor 300 during a centrifuge operation. The number of receptacles 308 (e.g., twelve) selected may be based on the number of samples being processed so long as the rotor 300 is balanced during operation. The housing 302 of the rotor 300 may be fabricated from any suitable material, such as plastic, aluminum, steel, or another metal. The housing 302 of the rotor 300 may be transparent or translucent so that an operator of the centrifuge system may visually identify or otherwise inspect the samples being processed by the rotor.

Figure 27:
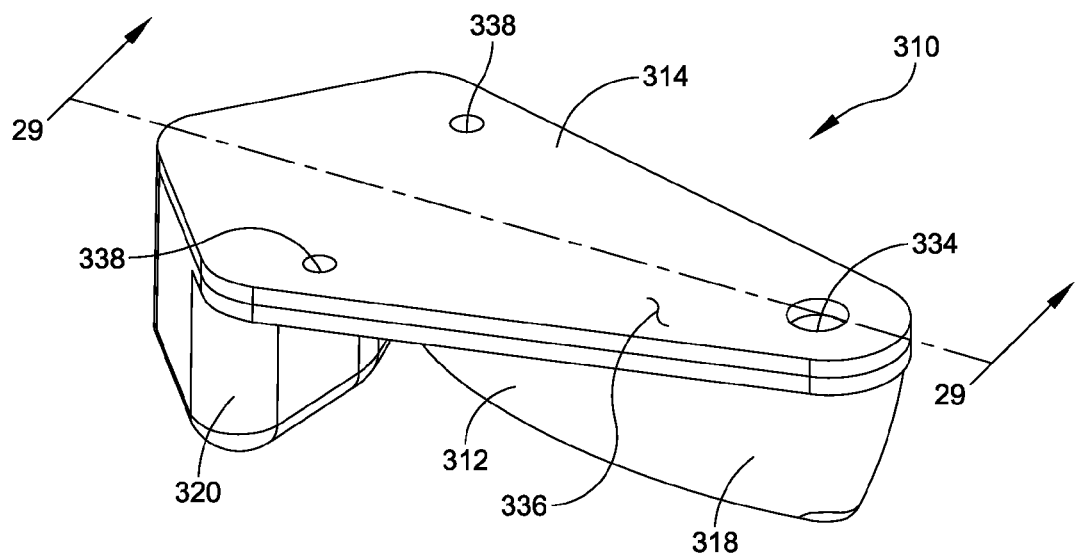
FIG. 27 is a perspective view of a disposable sample container of an embodiment of the disclosure.
Figure 28:
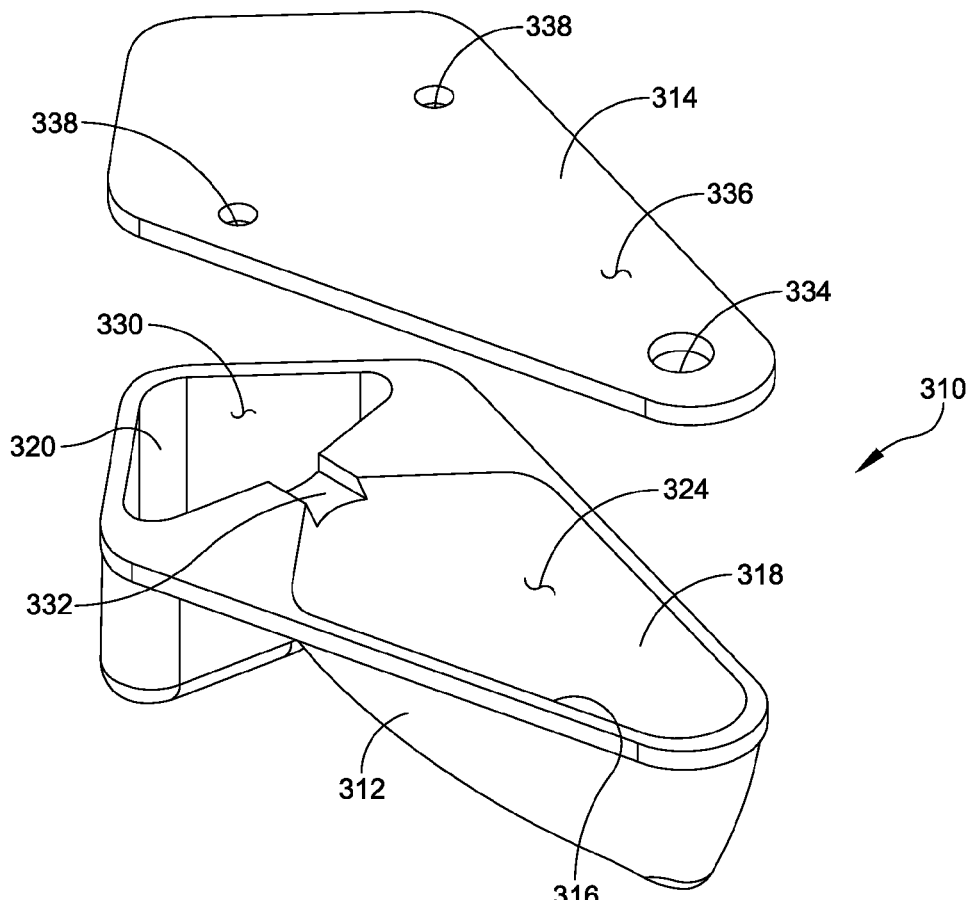
FIG. 28 is a perspective view of the disposable sample container shown in FIG. 27 with a cover removed from the disposable sample container.
Figure 29:
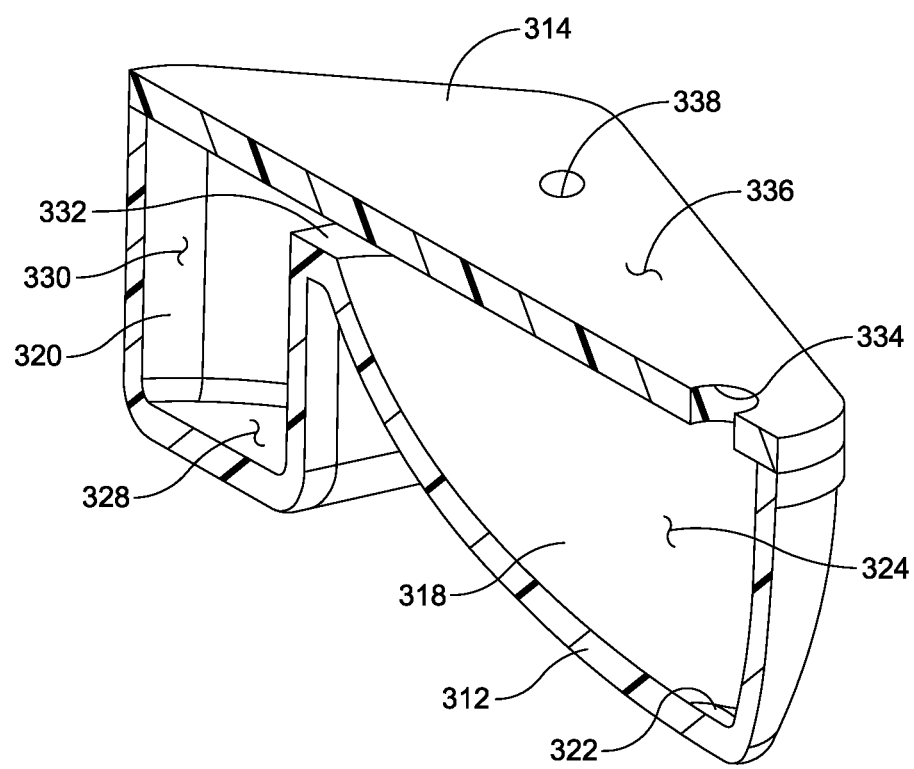
FIG. 29 is a cross-sectional perspective view of the disposable sample container taken along line 29-29 in FIG. 27.

Referring to FIGS. 27-29, a disposable sample container, generally indicated at 310, is provided to receive biological samples and process such samples when inserting the sample container into the rotor 300 shown in FIG. 26. The number of sample containers 310, e.g., twelve, may be selected to match the number of receptacles in the rotor 300. In one embodiment, the sample container 310 includes a main body 312 configured to receive the biological sample as described and a separate cover 314 that is sized to completely cover an opening 316 of the main body 312. As with some of the chamber designs described above, the main body 312 of the sample container includes two primary portions, a first chamber portion 318 and a second chamber portion 320 in fluid communication with the first chamber portion. The first chamber portion 318 includes a bottom wall portion 322 and a side wall portion 324. Similarly, the second chamber portion 320 includes a bottom wall portion 328, and a side wall portion 330. A channel 332 provides fluid communication between the first chamber portion 318 and the second chamber portion 320.

The cover 314 includes an inlet/outlet opening 334 formed in the cover over the first chamber portion 318 when positioning the cover over the main body 312. The cover 314 further has a flat surface 336 that is configured to be used with a robotic vacuum cup handling mechanism (not shown) to pick up and deposit the sample container 310. In other embodiments, the flat surface 336 of the cover 314 may be configured with pin holes/wells, each indicated at 338, which may be used with a robotic pin tool handling mechanism (not shown). With this arrangement, the robotic pin tool may be installed with one or more pins having diameters that are slightly larger than the pin holes in the cover 314. The pin tool may plunge down to pick up the sample container 310, and may later release the sample container with a release mechanism.

As shown in FIGS. 28 and 29, the channel 332 of the sample container 310 has a small cross sectional area that restricts the free flow of fluid from the first chamber portion 318 to the second chamber portion 320. In one embodiment, the second chamber portion 320 is disposed generally below the channel connecting the first chamber portion 318 and the second chamber portion. In addition, the second chamber portion 320 has a theoretical fill line disposed generally below the channel 332. As described above, the theoretical fill line represents a volume created by the second chamber portion 320 in which material is retained within the second chamber portion below the channel 332. The configuration of the sample container 310 is such that when a centrifuge operation takes place, a first complex fluid component is retained within the first chamber portion 318 and a second complex fluid component is retained within the second chamber portion 320.

The sample container 310 may be fabricated from any suitable material, such as hard/rigid or soft/flexible plastic. For example, sample containers made from flexible plastic may be formed into a desired shape, fit well inside a receptacle of the rotor, and may be well supported and/or contained inside the receptacle during a centrifugation process.

Figure 30:
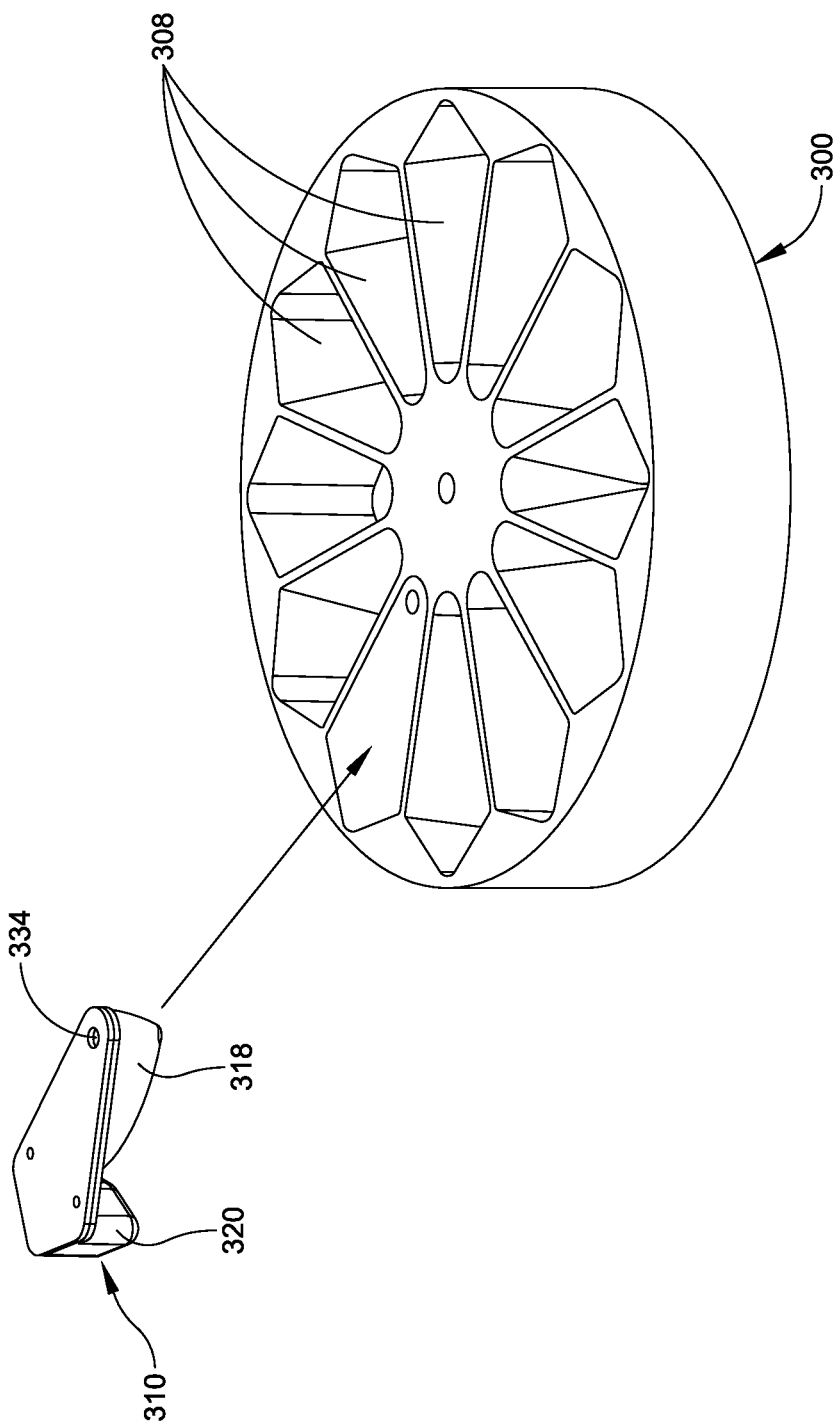
FIG. 30 is a perspective view of the disposable sample container being inserted into the rotor.

Referring to FIG. 30, the sample container 310 is inserted in one of the receptacles 308 of the rotor 300. As described, twelve such sample containers 310 may be inserted into respective receptacles 308 of the rotor 300. The arrangement is such that each sample container 310 extends along a respective radial axis extending from the central opening 304 to the periphery of the rotor 300. When installed, the first chamber portion 318 of the sample container 310 is disposed inboard with respect to the second chamber portion 320, with the inlet/outlet opening 334 being disposed toward the center of the rotor 300.

Figure 31:
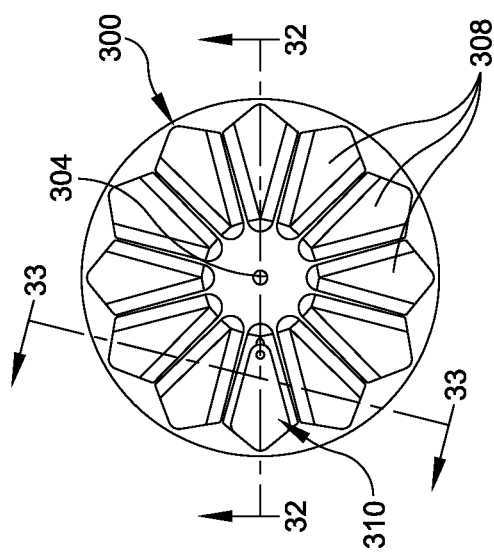
FIG. 31 is a top view of the disposable sample container inserted into the rotor as shown in FIG. 30.
Figure 33:
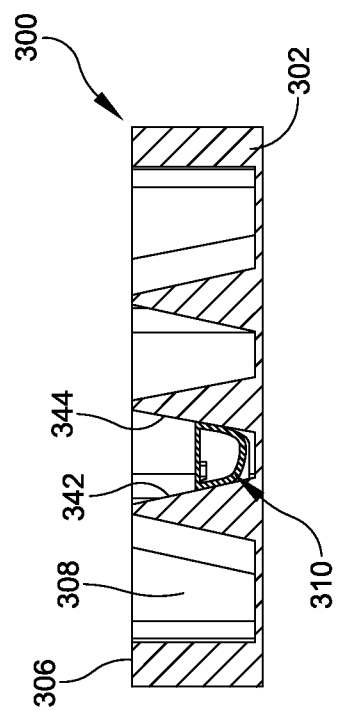
FIG. 33 is a cross-sectional view taken along line 33-33 in FIG. 31.
Figure 32:
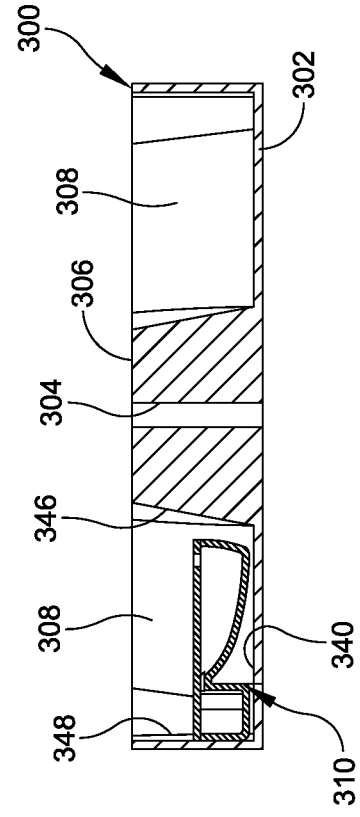
FIG. 32 is a cross-sectional view taken along line 32-32 in FIG. 31.

Referring to FIGS. 31-33, each receptacle 308 of the rotor 300 is sized to receive the sample container 310. Specifically, each receptacle 308 of the rotor 300 includes a bottom wall 340, two tapered side walls 342, 344, which are sized to guide and snugly fit the sample container 310 so that the sample container rests on the bottom wall with the side walls engaging the side walls of the sample container, and two end walls 346, 348. The tapered side walls 342, 344 may also assist in accommodate and register different sizes of sample containers 310 within the rotor 300. End wall 346 is slightly tapered while the opposite end wall 348 adjacent the outer periphery of the rotor 300 may be vertical or slightly tapered. This end wall 340 engages the sample container 310 to achieve solid contact and support of the sample container, particularly during a centrifugation process.

Figure 34:
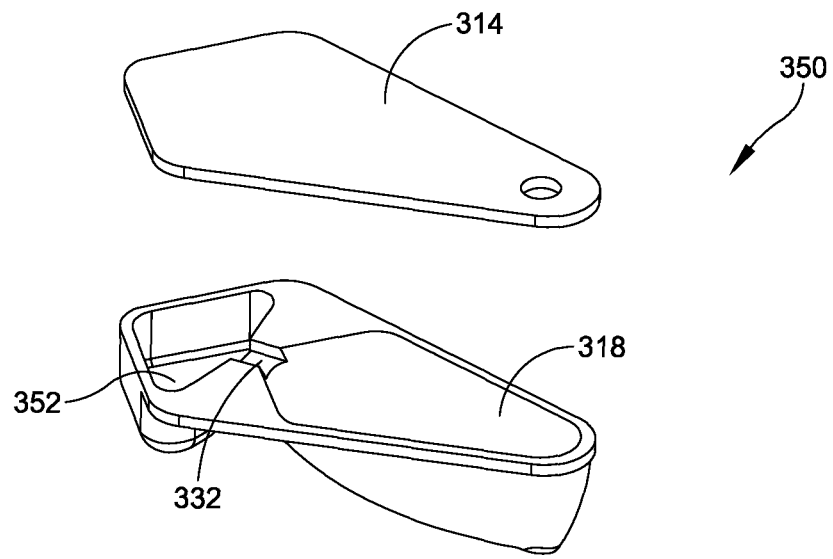
FIG. 34 is a perspective view of a disposable sample container of another embodiment of the disclosure.
Figure 35:
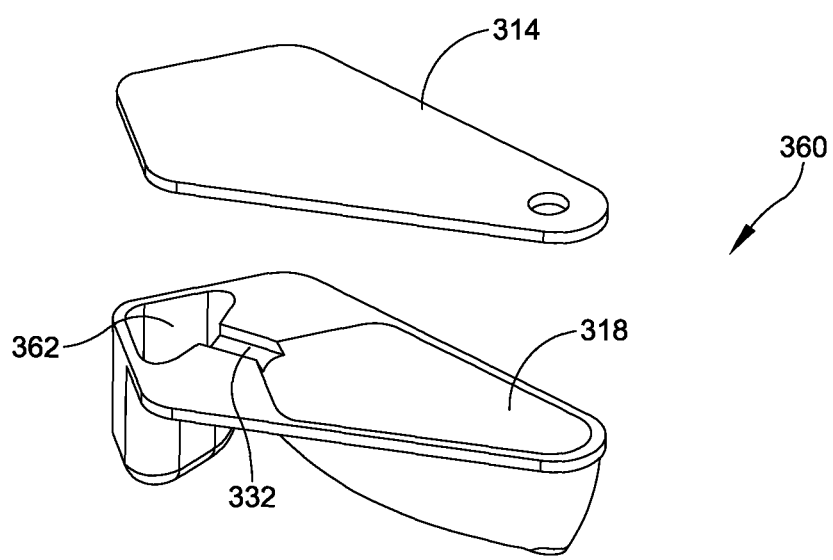
FIG. 35 is a perspective view of a disposable sample container of another embodiment of the disclosure.

Referring to FIGS. 34 and 35, the disposable sample container may be designed to reduce the volume of the second chamber portion to accommodate a smaller loading volume or a complex fluid with different composition (e.g., lower hematocrit whole blood). For example, FIG. 34 illustrates a disposable sample container 350 having a second chamber portion 352 that is shallower than the second chamber portion 320 of the sample container 310 to reduce the volume of material that can be contained in the second chamber portion. In another example, FIG. 35 illustrates a disposable sample container 360 having a second chamber portion 362 that is moved closer to the outer periphery of the sample container to reduce the volume of material contained in the second chamber portion.

Figure 36:
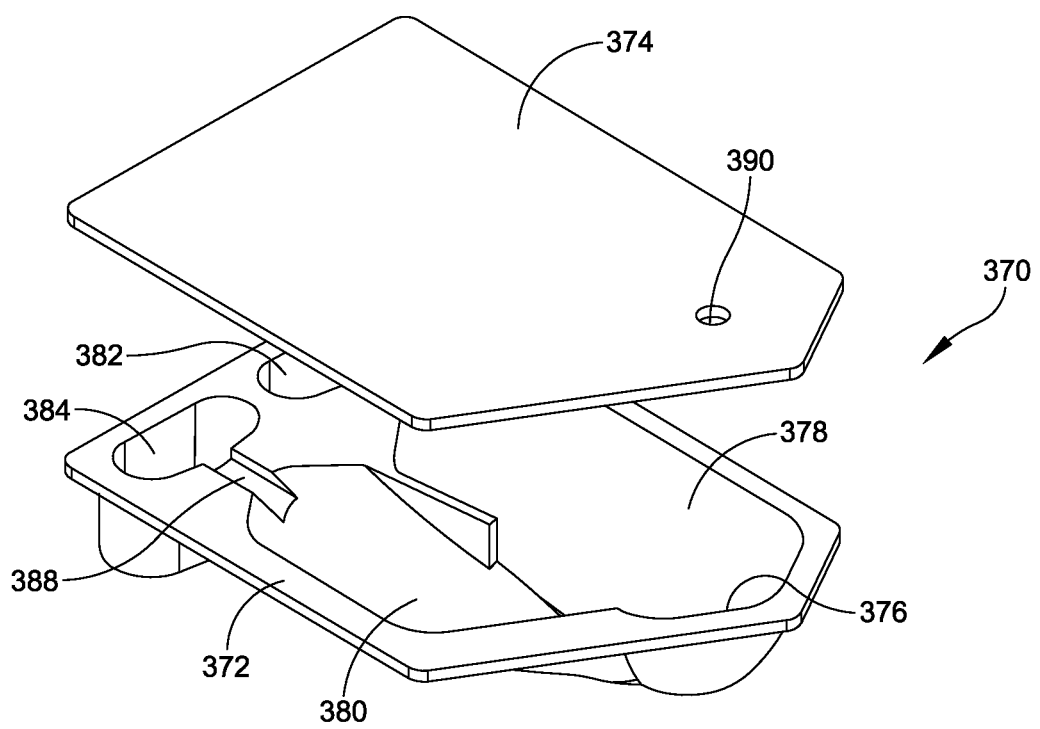
FIG. 36 is a perspective view of a disposable sample container of another embodiment of the disclosure.

Referring to FIGS. 36 and 37A-37G, the disposable container may be designed to process two different possible desired volumes of blood. For example, it may be desirable to conduct two or more tests, which may need different amounts of plasma, but to us the sample containers. Referring to FIG. 36, a disposable sample container, generally indicated at 370, is provided to receive biological samples and process such samples when inserting the sample container into a rotor specifically designed to receive the sample containers. In one embodiment, the sample container 370 includes a main body 372 configured to receive the biological sample as described and a separate cover 374 that is sized to completely cover an opening 376 of the main body.

Unlike the chamber designs described above, the main body 372 of the sample container includes two inlet chamber portions 378, 380 and two outlet chamber portions 382, 384 in fluid communication with their respective first chamber portions. As shown, the first inlet chamber portion 378 is in fluid communication with the second inlet chamber portion 380. A channel 386 provides fluid communication between the first inlet chamber portion 378 (the top inlet chamber portion as shown in FIG. 37A) and the first outlet chamber portion 380. Similarly, another channel 388 provides fluid communication between the second inlet chamber portion 380 (the bottom inlet chamber portion as shown in FIG. 37A) and the second outlet chamber portion 384. The cover 374 includes an inlet/outlet opening 390 formed in the cover over the first inlet chamber portion 378 when positioning the cover over the main body 372.

With the disposable sample container 370 shown in FIGS. 36 and 37A-37G, the two inlet chamber portions 378, 380 are connected with their respective channels 386, 388 in a manner similar to other described embodiments. If a small volume of complex fluid is deposited in the first inlet chamber portion, then the fluid level under gravity and the fluid level under centrifugation are both such that fluid never enters the second inlet chamber portion and the second outlet chamber portion. However, if a larger volume of complex fluid is deposited, then the fluid level under centrifugation is such that the fluid reaches an "overflow" condition, which allows fluid to drain into the second inlet and outlet chamber portions 380, 384. Optionally, this sample container design may or may not allow fluid to flow into the second chamber under gravity before centrifugation. After centrifugation, gravity pulls the plasma from both inboard inlet chamber portions 378, 380 to the same inlet/outlet.

By adjusting the design shown in FIGS. 36 and 37A-37G, one skilled in the art may design a sample chamber to process either of any two chosen volumes of fluid, a first volume and a second potentially different volume. Using the concept and approach shown in FIGS. 36 and 37A-37G, one skilled in the art may readily add further chambers to process each of three or more possible volumes.

As can be seen from the above description, embodiments of the present disclosure have several different aspects and features, which are not limited to the specific chamber shown in the attached drawings or to the specific procedures discussed. Variations of these features may be embodied in other structures for carrying out other procedures for blood separation, processing or collection. For example, any of the chambers shown and described herein may be provided with vent channels and/or outlet channels depending on the shape and size of the channel.

Having thus described several aspects of at least one embodiment of this disclosure, it is to be appreciated various alterations, modifications, and improvements will readily occur to those skilled in the art. Such alterations, modifications, and improvements are intended to be part of this disclosure, and are intended to be within the spirit and scope of the disclosure. Accordingly, the foregoing description and drawings are by way of example only.

The invention claimed is:

1. A rotor for use in a centrifuge system configured to spin the rotor, the rotor comprising:
   a housing configured to be secured by the centrifuge system; and
   at least one chamber formed in the housing, the at least one chamber including a first chamber portion having an outlet port formed therein and a second chamber portion in fluid communication with the outlet port of the first chamber portion, the first chamber portion having a bottom wall portion, the second chamber portion having a bottom wall portion disposed below the bottom wall portion of the first chamber portion, the bottom wall portion of the first chamber portion forming part of the outlet port that communicates with a channel connecting the first chamber portion to an inlet port provided in the second chamber portion, the second chamber portion being disposed generally below the outlet port of the first chamber portion, the first chamber portion being disposed inboard with respect to the second chamber portion, the bottom wall portion of the first chamber portion sloping towards the outlet port of the first chamber portion, the channel having a height and a width that are smaller than a height and a width of the first chamber portion at a location inboard of the outlet port to restrict the free flow of fluid from the first chamber portion to the second chamber portion.

2. The rotor of claim 1, wherein the first chamber portion and the second chamber portion are configured so that when a centrifuge operation takes place, a first complex fluid component is substantially retained in the first chamber portion and a second complex fluid component is substantially retained in the second chamber portion.

3. The rotor of claim 1, wherein the bottom wall portion of the first chamber portion slopes upwardly to the outlet port of the first chamber portion.

4. The rotor of claim 3, wherein the first chamber portion of the at least one chamber includes an inlet/outlet opening configured to receive a complex fluid.

5. The rotor of claim 4, wherein the first chamber portion and the second chamber portion are configured so that when a centrifuge operation takes place, a first complex fluid component is substantially retained in the first chamber portion and a second complex fluid component is retained in the second chamber portion.

6. The rotor of claim 3, wherein the bottom wall portion of the first chamber portion is configured to direct fluid to the outlet channel.

7. The rotor of claim 1, wherein the first chamber portion and the second chamber portion extend along a radial axis of the rotor, the first chamber portion and the second chamber portion being configured so that when a centrifuge operation takes place, a first complex fluid component is retained in the first chamber portion and a second complex fluid component is retained in the second chamber portion.

8. The rotor of claim 1, wherein the second chamber portion has a fill line disposed generally below the outlet port of the first chamber portion, the fill line representing a volume created by the second chamber portion in which material is retained within the second chamber portion below the outlet port.

9. The rotor of claim 1, wherein the first chamber portion includes a wall that slopes toward the outlet port of the first chamber portion.

* * * * *

UNITED STATES PATENT AND TRADEMARK OFFICE
CERTIFICATE OF CORRECTION

PATENT NO. : 9,081,022 B2  
APPLICATION NO. : 13/363938  
DATED : July 14, 2015  
INVENTOR(S) : Matthew K. Runyon et al.

It is certified that error appears in the above-identified patent and that said Letters Patent is hereby corrected as shown below:

In the Specification:
Column 10, line 9, replace "bather" with --barrier--.

Signed and Sealed this
Twelfth Day of April, 2016

Michelle K. Lee
*Director of the United States Patent and Trademark Office*